US012637499B2

(12) United States Patent
Kitamura

(10) Patent No.: US 12,637,499 B2
(45) Date of Patent: May 26, 2026

(54) ADRENOMEDULLIN ANALOG, METHOD FOR PRODUCING THE SAME, AND PHARMACEUTICAL USE THEREOF

(71) Applicant: University of Miyazaki, Miyazaki (JP)

(72) Inventor: Kazuo Kitamura, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 323 days.

(21) Appl. No.: 17/916,062

(22) PCT Filed: Apr. 2, 2021

(86) PCT No.: PCT/JP2021/014296
§ 371 (c)(1),
(2) Date: Sep. 30, 2022

(87) PCT Pub. No.: WO2021/201271
PCT Pub. Date: Oct. 7, 2021

(65) Prior Publication Data
US 2023/0174607 A1      Jun. 8, 2023

(30) Foreign Application Priority Data

Apr. 2, 2020    (JP) ................................. 2020-066608

(51) Int. Cl.
C07K 14/575      (2006.01)
A61K 38/22      (2006.01)
A61P 31/16      (2006.01)

(52) U.S. Cl.
CPC ............ C07K 14/575 (2013.01); A61K 38/22 (2013.01); A61P 31/16 (2018.01)

(58) Field of Classification Search
None
See application file for complete search history.

(56) References Cited

U.S. PATENT DOCUMENTS

| 5,639,855 | A | 6/1997 | Kitamura et al. | |
| 6,440,421 | B1 * | 8/2002 | Cornish | A61P 11/08 |
| | | | | 530/328 |
| 7,547,553 | B2 * | 6/2009 | Bergmann | G01N 33/6896 |
| | | | | 436/811 |
| 10,335,455 | B2 * | 7/2019 | Kitamura | A61P 1/04 |
| 2007/0161555 | A1 | 7/2007 | Yanagita | |
| 2013/0296260 | A1 | 11/2013 | Kitamura et al. | |
| 2018/0170991 | A1 | 6/2018 | Kitamura et al. | |

| 2018/0193422 | A1 * | 7/2018 | Shandler | A61K 38/2278 |
| 2018/0264123 | A1 | 9/2018 | Kitamura et al. | |
| 2021/0115103 | A1 | 4/2021 | Kitamura et al. | |

FOREIGN PATENT DOCUMENTS

| EP | 1 205 185 | A1 | 5/2002 | |
| EP | 3 127 914 | A1 | 2/2017 | |
| JP | 2774769 | B2 | 7/1998 | |
| JP | 4830093 | B2 | 12/2011 | |
| JP | 5954736 | B2 | 7/2016 | |
| WO | 00/78339 | A1 | 12/2000 | |
| WO | WO-2009043481 | A2 * | 4/2009 | A23L 33/18 |
| WO | 2015/141819 | A1 | 9/2015 | |
| WO | 2017/047788 | A1 | 3/2017 | |
| WO | 2018/181638 | A1 | 10/2018 | |

OTHER PUBLICATIONS

K0I035_MARMO dowloaded from https://www.uniprot.org/uniprotkb/K0I035/entry on Jun. 23, 2025 (Year: 2025).*
Pro-adrenomedullin precursor [*Homo sapiens*] NCBI Reference Sequence: NP_001115.1, downloaded on Dec. 1, 2025 from https://www.ncbi.nlm.nih.gov/protein/NP_001115.1?report=genbank&log$=protalign&blast_rank=1&RID=JVRDHH52014 (Year: 2025).*
Extended European Search Report dated Mar. 20, 2024, issued in corresponding European Patent Application No. 21778972.6.
Kitamura et al., "Adrenomedullin: A Novel Hypotensive Peptide Isolated from Human Pheochromocytoma," Biochemical and Biophysical Research Communications, 192 (2): 553-560 (1993).
Eguchi et al., "Structure-activity relationship of adrenomedullin, a novel vasodilatory peptide, in cultured rat vascular smooth muscle cells," Endocrinology, 135 (6): 2454-5458 (1994).
International Search Report issued in corresponding International Patent Application No. PCT/JP2021/014296 dated May 11, 2021.

* cited by examiner

*Primary Examiner* — Christina Bradley
(74) *Attorney, Agent, or Firm* — Morgan, Lewis & Bockius LLP

(57) ABSTRACT

The disclosure provides a compound or a salt thereof, or a solvate thereof, wherein the compound is a peptide selected from the group consisting of: (a) a peptide consisting of an amino acid sequence of SEQ ID NO: 3 wherein one to three amino acid residues are substituted or deleted; (b) a peptide having a disulfide bond formed by cysteine residues at positions 4 and 9 of (a); (c) a peptide wherein the disulfide bond of (b) is substituted with an ethylene group; (d) a peptide wherein one to three amino acid residues of any of (a) to (c) are deleted or added; (e) a peptide wherein any of (a) to (d) is amidated at the C-terminus thereof; and (f) a peptide wherein any of (a) to (d) has a glycine residue added to the C-terminus thereof, and the use thereof.

23 Claims, 11 Drawing Sheets
Specification includes a Sequence Listing.

ADRENOMEDULLIN ANALOG, METHOD FOR PRODUCING THE SAME, AND PHARMACEUTICAL USE THEREOF

SEQUENCE LISTING SUBMISSION VIA EFS-WEB

A computer readable text file, entitled "SequenceListing.txt" created on Sep. 29, 2022, with a file size of 5,174 bytes and contains the sequence listing for this application and is hereby incorporated by reference in its entirety.

TECHNICAL FIELD

The present invention relates to a novel adrenomedullin analog, a method for producing the same, and pharmaceutical use thereof.

BACKGROUND ART

Adrenomedullin (hereinafter, also described as "AM") is a bioactive peptide which was isolated and identified from pheochromocytoma in 1993 (Non Patent Literature 1). At the beginning of the discovery, AM was found to exert a strong vasodilatory hypotensive effect. For example, Patent Literature 1 describes a peptide having a blood pressure-lowering effect that comprises the amino acid sequence of human AM.

Subsequent studies revealed that AM exerts diverse pharmacological effects such as a cardiovascular protective effect, an anti-inflammatory effect, an angiogenic effect, and a tissue repair promoting effect. In an effort to apply the pharmacological effects of AM to treatment of disease, administration of AM to patients with different disease has been attempted. AM is expected to be useful as a therapeutic agent for inflammatory bowel disease, pulmonary hypertension, a peripheral vascular disease, or acute myocardial infarction, among others.

For example, Patent Literature 2 describes an agent for preventing or treating nonbacterial inflammatory bowel disease wherein the agent comprises, as an active ingredient, adrenomedullin or a derivative thereof that has an activity to suppress nonbacterial inflammation, or a salt thereof that has an activity to suppress nonbacterial inflammation.

Patent Literature 3 describes a method for preventing or treating an inflammatory bowel disease for which the use of a steroid formulation, an immunosuppressant, or a biological formulation is difficult or insufficiently effective in a patient in need of prevention or treatment of the inflammatory bowel disease, the method comprising administering an effective amount of adrenomedullin, a derivative thereof having an activity of suppressing inflammation, or a salt of the adrenomedullin or the derivative having an activity of suppressing inflammation, to the patient.

Since AM is a peptide, AM has a short half-life due to a metabolism in a living body (such as in blood). Accordingly, in administering AM to subjects, it is needed to select a sustainable administration method such as continuous intravenous infusion. AM has a strong vasodilatory effect, in addition to pharmacological effects such as a cardiovascular protective effect, an anti-inflammatory effect, an angiogenic effect, and a tissue repair promoting effect. This strong vasodilatory effect may cause unwanted side effects such as excessive decreased blood pressure when AM is administered to subjects. In view of those problems, adrenomedullin derivatives have been developed which are sustainable for a long period and capable of substantially suppressing unwanted side effects while maintaining pharmacological effects of adrenomedullin (Patent Literatures 4 to 6).

CITATION LIST

Patent Literature

Patent Literature 1: JP Patent No. 2774769
Patent Literature 2: JP Patent No. 4830093
Patent Literature 3: JP Patent No. 5954736
Patent Literature 4: International Publication No. WO 2015/141819
Patent Literature 5: International Publication No. WO 2017/047788
Patent Literature 6: International Publication No. WO 2018/181638

Non Patent Literature

Non Patent Literature 1: Kitamura K, Kangawa K, Kawamoto M, Ichiki Y, Nakamura S, Matsuo H, Eto T. Adrenomedullin: a novel hypotensive peptide isolated from human pheochromocytoma. Biochem Biophys Res Commun, 30 Apr. 1993, Volume 192, Issue 2, pp. 553-560

SUMMARY OF INVENTION

Technical Problem

As described above, various adrenomedullin derivatives have been developed in order to improve the pharmacokinetics of adrenomedullin from the viewpoint of improvement in sustainability in a living body. However, known adrenomedullin derivatives suffer from a problem of reduced binding affinity for the adrenomedullin receptor as compared with the parent compound adrenomedullin. Because the pharmacological effects of adrenomedullin or a derivative thereof develop through the binding of the compound to the adrenomedullin receptor, adrenomedullin derivatives having binding affinity lower than that of adrenomedullin may have reduced pharmacological effects as compared with adrenomedullin, as well.

The invention, therefore, is intended to provide novel adrenomedullin analogs that exhibit high biological stability in administering to subjects while maintaining pharmacological effects of the parent compound adrenomedullin.

Solution to Problem

The present inventors conducted various investigations of means to solve the problems described above. On the basis of the structure of a decomposition product of adrenomedullin in blood, the present inventors developed novel adrenomedullin analogs obtained by substituting or deleting some amino acid residues of a peptide having the same amino acid sequence as an amino acid sequence at positions 13 to 52 of natural human adrenomedullin. The present inventors have found that these novel adrenomedullin analogs exhibit significantly superior pharmacokinetics, for example, with respect to biological stability, to adrenomedullin while maintaining pharmacological effects substantially equivalent to those of the parent compound adrenomedullin. The present inventors have achieved the invention based on the finding described above.

That is to say, the invention includes the following aspects and embodiments.

(1) A compound or a salt thereof, or a solvate thereof, wherein the compound is a peptide selected from the group consisting of:

(a) a peptide consisting of an amino acid sequence of SEQ ID NO: 3 wherein one to three amino acid residues are substituted or deleted;

(b) a peptide having a disulfide bond formed by cysteine residues at positions 4 and 9 of the peptide of (a);

(c) a peptide wherein the disulfide bond of the peptide of (b) is substituted with an ethylene group;

(d) a peptide wherein one to three amino acid residues of any of the peptides of (a) to (c) are deleted or added;

(e) a peptide wherein any of the peptides of (a) to (d) is amidated at the C-terminus thereof; and (f) a peptide wherein any of the peptides of (a) to (d) has a glycine residue added to the C-terminus thereof.

(2) The compound according to the embodiment (1) or a salt thereof, or a solvate thereof, wherein the peptide is a peptide selected from the group consisting of:

(a) a peptide consisting of an amino acid sequence of SEQ ID NO: 3 wherein one to three amino acid residues are substituted or deleted;

(b) a peptide having a disulfide bond formed by cysteine residues at positions 4 and 9 of the peptide of (a);

(d) a peptide wherein one to three amino acid residues of any of the peptides of (a) to (c) are deleted or added;

(e) a peptide wherein any of the peptides of (a) to (d) is amidated at the C-terminus thereof; and (f) a peptide wherein any of the peptides of (a) to (d) has a glycine residue added to the C-terminus thereof.

(3) The compound according to the embodiment (1) or (2) or a salt thereof, or a solvate thereof, wherein, in the peptide of (a), one amino acid residue is substituted or deleted.

(4) The compound according to the embodiment (3) or a salt thereof, or a solvate thereof, wherein, in the peptide of (a), an amino acid residue at position 32 or 33 is substituted or deleted.

(5) The compound according to any of the embodiments (1) to (4) or a salt thereof, or a solvate thereof, wherein the peptide of (a) is a peptide consisting of an amino acid sequence of any of SEQ ID NOs: 4 to 11.

(6) The compound according to any of the embodiments (1) to (5) or a salt thereof, or a solvate thereof, wherein the compound is a peptide consisting of an amino acid sequence of any of SEQ ID NOs: 4 to 11, being amidated at the C-terminus thereof, and having a disulfide bond formed by cysteine residues at positions 4 and 9.

(7) A method for producing the compound according to any of the embodiments (1) to (6) or a salt thereof, or a solvate thereof, the method comprising: a peptide chain synthesis step of synthesizing a peptide chain having an amino acid sequence of the compound according to any of the embodiments (1) to (6) by peptide synthesis on solid phase system or in liquid phase system.

(8) A medicament comprising the compound according to any of the embodiments (1) to (6) or a pharmaceutically acceptable salt thereof, or a pharmaceutically acceptable solvate thereof as an active ingredient.

(9) The medicament according to the embodiment (8), for use in the prevention or treatment of cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

(10) An agent for preventing or treating cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection, wherein the agent comprises the compound according to any of the embodiments (1) to (6) or a pharmaceutically acceptable salt thereof, or a pharmaceutically acceptable solvate thereof as an active ingredient.

(11) A pharmaceutical composition comprising the compound according to any of the embodiments (1) to (6) or a pharmaceutically acceptable salt thereof, or a pharmaceutically acceptable solvate thereof and one or more pharmaceutically acceptable carriers.

(12) The pharmaceutical composition according to the embodiment (11) for use in the prevention or treatment of cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

(13) A method for preventing or treating one or more conditions, diseases, and/or disorders selected from the group consisting of cardiovascular diseases, brain and nervous system diseases, gastrointestinal diseases, endocrine metabolic diseases, respiratory diseases, and other diseases, the method comprising administering an effective amount of the compound according to any of the embodiments (1) to (6) or a pharmaceutically acceptable salt thereof, or a pharmaceutically acceptable solvate thereof to a subject in need of prevention or treatment of the conditions, diseases, and/or disorders.

(14) The method according to the embodiment (13), wherein the one or more conditions, diseases, and/or disorders are cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

(15) The compound according to any of the embodiments (1) to (6) or a pharmaceutically acceptable salt thereof, or a pharmaceutically acceptable solvate thereof for use in the prevention or treatment of one or more conditions, diseases, and/or disorders.

(16) The compound for use according to the embodiment (15) or a pharmaceutically acceptable salt thereof, or a pharmaceutically acceptable solvate thereof, wherein the one or more conditions, diseases, and/or disorders are cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

(17) Use of the compound according to any of the embodiments (1) to (6) or a pharmaceutically acceptable salt thereof, or a pharmaceutically acceptable solvate thereof in the manufacture of a medicament for the prevention or treatment of one or more conditions, diseases, and/or disorders.

(18) Use of the compound according to any of the embodiments (1) to (6) or a pharmaceutically acceptable salt thereof, or a pharmaceutically acceptable solvate thereof for the prevention or treatment of one or more conditions, diseases, and/or disorders.

(19) The use according to the embodiment (17) or (18), wherein the one or more conditions, diseases, and/or disorders are cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

Advantageous Effects of Invention

The invention can provide novel adrenomedullin analogs that exhibit high biological stability in administering to subjects while maintaining pharmacological effects of the parent compound adrenomedullin.

The present specification includes contents described in the specification and/or drawings of Japanese patent application No. 2020-066608 to which the present application claims priority.

DESCRIPTION OF EMBODIMENTS

<1. Adrenomedullin Analog>

Figure 1:
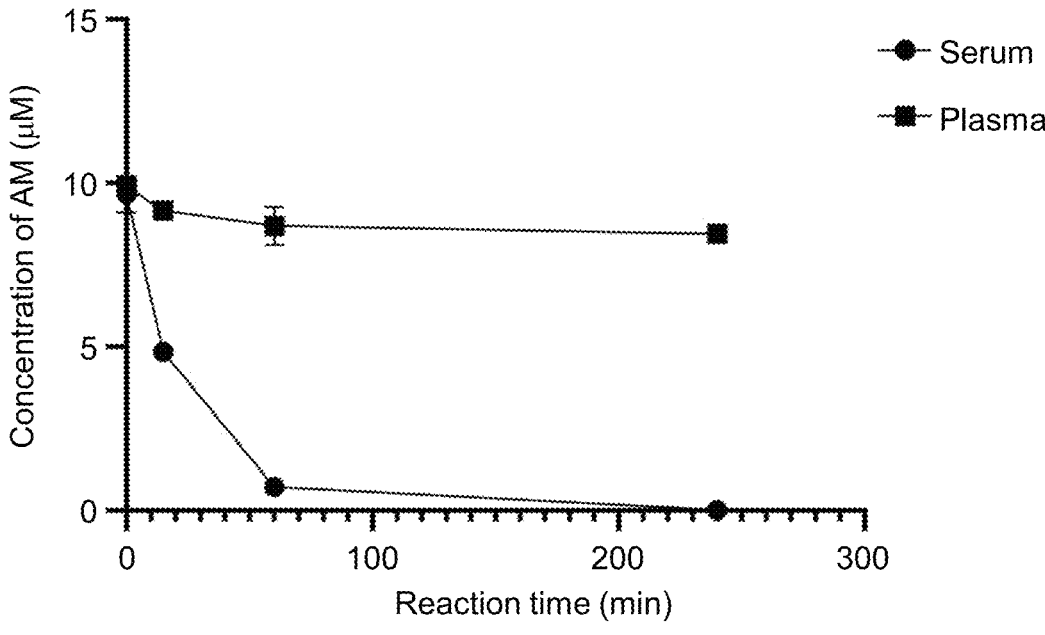
FIG. 1 shows time course of concentration of AM contained in samples of a rection mixture with serum or plasma in Experiment I. In the figure, the abscissa represents reaction time (min), and the ordinate represents concentration of AM (UM).

Adrenomedullin (AM) is a bioactive peptide which was isolated and identified from human pheochromocytoma in 1993 (SEQ ID NO: 1, Non Patent Literature 1). A peptide consisting of the amino acid sequence of SEQ ID NO: 1, being amidated at the C-terminus thereof, and having a disulfide bond formed by two cysteine residues at positions 16 and 21 in the amino acid sequence represents a mature natural human adrenomedullin (hereinafter, also described as "hAM(1-52)"). A peptide consisting of the amino acid sequence of SEQ ID NO: 1 represents a form of natural human adrenomedullin prior to post-translational modification including C-terminal amidation and disulfide bond formation by cysteine residues (i.e., an immature form).

hAM(1-52)

(SEQ ID NO: 1)
Y-R-Q-S-M-N-N-F-Q-G-L-R-S-F-G-C-R-F-G-T-C-T-V-Q-K-

L-A-H-Q-I-Y-Q-F-T-D-K-D-K-D-N-V-A-P-R-S-K-I-S-P-Q-

G-Y-CONH$_2$

At the beginning of the discovery, AM was found to exert a strong vasodilatory hypotensive effect. Subsequent studies revealed that AM exerts diverse pharmacological effects such as a cardiovascular protective effect, an anti-inflammatory effect, an angiogenic effect, and a tissue repair promoting effect. In an effort to apply the pharmacological effects of AM to treatment of disease, administration of AM to patients with different diseases has been attempted.

Since AM is a peptide, AM has a short half-life due to a metabolism in a living body (such as in blood). AM has a strong vasodilatory effect, in addition to pharmacological effects such as a cardiovascular protective effect, an anti-inflammatory effect, an angiogenic effect, and a tissue repair promoting effect. This strong vasodilatory effect may cause unwanted side effects such as excessive decreased blood pressure when AM is administered to subjects. In view of those problems, various adrenomedullin derivatives have been developed which are sustainable for a long period (Patent Literatures 4 to 6). However, known AM derivatives suffer from a problem of reduced binding affinity for the adrenomedullin receptor as compared with the parent compound AM. Because the pharmacological effects of AM or a derivative thereof develop through the binding of these compounds to the adrenomedullin receptor, AM derivatives having binding affinity lower than that of AM may have reduced pharmacological effects as compared with AM, as well.

The present inventors analyzed a decomposition product of AM in blood to find that a peptide consisting of amino acid residues at positions 13 to 44 of natural human AM (hAM(1-52)) (hAM(13-44), SEQ ID NO: 2) is generated as a decomposition product. On the basis of the result, the present inventors developed novel AM analogs obtained by substituting or deleting some amino acid residues of a peptide consisting of amino acid residues at positions 13 to 52 of natural human AM, being amidated at the C-terminus thereof, and having a disulfide bond formed by two cysteine residues at positions 16 and 21 in the amino acid sequence (hAM(13-52), SEQ ID NO: 3). The present inventors have found that these novel AM analogs exhibit significantly superior pharmacokinetics, for example, with respect to biological stability, to AM while maintaining pharmacological effects substantially equivalent to those of the parent compound AM.

```
hAM(13-44)
                                      (SEQ ID NO: 2)
S-F-G-C-R-F-G-T-C-T-V-Q-K-L-A-H-Q-I-Y-Q-F-T-D-K-D-

K-D-N-V-A-P-R-COOH hAM(13-52)
                                      (SEQ ID NO: 3)
S-F-G-C-R-F-G-T-C-T-V-Q-K-L-A-H-Q-I-Y-Q-F-T-D-K-D-

K-D-N-V-A-P-R-S-K-I-S-P-Q-G-Y-CONH₂
```

Therefore, an aspect of the invention relates to a compound or a salt thereof, or a solvate thereof, wherein the compound is a peptide selected from the group consisting of:
    (a) a peptide consisting of an amino acid sequence of SEQ ID NO: 3 wherein one to three amino acid residues are substituted or deleted;
    (b) a peptide of (a) having a disulfide bond formed by cysteine residues at positions 4 and 9 of the peptide of (a);
    (c) a peptide wherein the disulfide bond of the peptide of (b) is substituted with an ethylene group;

(d) a peptide wherein one to three amino acid residues of any of the peptides of (a) to (c) are deleted or added;
    (e) a peptide wherein any of the peptides of (a) to (d) is amidated at the C-terminus thereof; and
    (f) a peptide wherein any of the peptides of (a) to (d) has a glycine residue added to the C-terminus thereof. Herein, the compound or a salt thereof, or a solvate thereof is also described as "adrenomedullin analog" or "AM analog".

In the mature human AM (hAM(1-52)), the cyclic structure in which the cysteine residues at positions 16 and 21 form a disulfide bond, and the C-terminal amide structure are both essential for the adrenomedullin activity, whereas the peptide structure consisting of amino acid residues at positions 1 to 12 of hAM(1-52) is not essential for the adrenomedullin activity (Eguchi S et al., Endocrinology. December 1994, Volume 135, Issue 6, p. 2454-8). In the compound according to the aspect, a peptide involved in (a) has cysteine residues at positions 16 and 21 forming a cyclic structure, and a tyrosine residue at position 52 forming a C-terminal amide structure, and has an amino acid sequence differing from that of natural human AM. A peptide involved in (e) has a cyclic structure and C-terminal amide structure essential for the adrenomedullin activity. Accordingly, the compound according to the aspect having the properties can maintain pharmacological effects substantially equivalent to those of the parent compound AM.

In the compound according to the aspect, the peptide is preferably a peptide selected from the group consisting of:
    (a) a peptide consisting of an amino acid sequence of SEQ ID NO: 3 wherein one to three amino acid residues are substituted or deleted;
    (b) a peptide having a disulfide bond formed by cysteine residues at positions 4 and 9 of the peptide of (a);
    (d) a peptide wherein one to three amino acid residues of any of the peptides of (a) to (c) are deleted or added;
    (e) a peptide wherein any of the peptides of (a) to (d) is amidated at the C-terminus thereof; and
    (f) a peptide wherein any of the peptides of (a) to (d) has a glycine residue added to the C-terminus thereof.

In the compound according to the aspect, the peptide is more preferably a peptide selected from the group consisting of:
    (a) a peptide consisting of an amino acid sequence of SEQ ID NO: 3 wherein one to three amino acid residues are substituted or deleted;
    (b) a peptide having a disulfide bond formed by cysteine residues at positions 4 and 9 of the peptide of (a);
    (d) a peptide wherein one to three amino acid residues of any of the peptides of (a) to (c) are deleted or added; and
    (e) a peptide wherein any of the peptides of (a) to (d) is amidated at the C-terminus thereof.

In the compound according to the aspect, the peptide is further preferably a peptide consisting of an amino acid sequence of SEQ ID NO: 3 wherein one to three amino acid residues are substituted or deleted, cysteine residues at positions 4 and 9 form a disulfide bond, one to three amino acid residues are deleted or added, and the C-terminus thereof is amidated.

In the peptide of (a), one to three amino acid residues are typically substituted or deleted, one or two amino acid residues are preferably substituted or deleted, and one amino acid residue is more preferably substituted or deleted. However, each of the substituted or deleted amino acid residues is neither the cysteine residue at position 4 nor that at position 9. In the embodiment, amino acid residues in the specified number among the amino acid residues at positions 1 to 3 and 10 to 40 are preferably substituted or deleted, amino acid residues in the specified number among the amino acid residues at positions 29 to 35 are more preferably substituted or deleted, and the amino acid residue at position 32 or 33 is further preferably substituted. Thrombin, a protease, is known to specifically recognize a sequence of several amino acid residues including arginine and selectively cleave the sequence (Gallwitz M, Enoksson M, Thorpe M, Hellman L, The Extended Cleavage Specificity of Human Thrombin. PLOS ONE, 2012, Volume 7, Issue 2, e31756. doi: 10.1371/journal.pone.0031756). The compound according to the embodiment can have a cyclic structure and C-terminal amide structure essential for the adrenomedullin activity even when the amino acid residues in the specified number at the specified positions have been substituted or deleted. Accordingly, the compound according to the embodiment having the properties can exhibit significantly superior pharmacokinetics, for example, with respect to biological stability, to the parent compound AM while maintaining pharmacological effects substantially equivalent to those of AM.

The peptide of (a) is preferably a peptide consisting of an amino acid sequence of any of SEQ ID NOs: 4 to 11. In the embodiment, a peptide consisting of an amino acid sequence of SEQ ID NO: 4 (i.e., an amino acid sequence such that arginine residue at position 32 (corresponding to position 44 of hAM(1-52)) of the amino acid sequence of SEQ ID NO: 3 is substituted with D-arginine (D-Arg)), being amidated at the C-terminus thereof, and having a disulfide bond formed by cysteine residues at positions 4 (corresponding to position 16 of hAM(1-52)) and 9 (corresponding to position 21 of hAM(1-52)) is described as [D-Arg-44]hAM(13-52). A peptide consisting of an amino acid sequence of SEQ ID NO: 5 (i.e., an amino acid sequence such that arginine residue at position 32 (corresponding to position 44 of hAM(1-52)) of the amino acid sequence of SEQ ID NO: 3 is substituted with L-lysine (Lys)), being amidated at the C-terminus thereof, and having a disulfide bond formed by cysteine residues at positions 4 (corresponding to position 16 of hAM(1-52)) and 9 (corresponding to position 21 of hAM(1-52)) is described as [Lys-44]hAM(13-52). A peptide consisting of an amino acid sequence of SEQ ID NO: 6 (i.e., an amino acid sequence such that arginine residue at position 32 (corresponding to position 44 of hAM(1-52)) of the amino acid sequence of SEQ ID NO: 3 is substituted with L-alanine (Ala)), being amidated at the C-terminus thereof, and having a disulfide bond formed by cysteine residues at positions 4 (corresponding to position 16 of hAM(1-52)) and 9 (corresponding to position 21 of hAM(1-52)) is described as [Ala-44]hAM(13-52). A peptide consisting of an amino acid sequence of SEQ ID NO: 7 (i.e., an amino acid sequence such that arginine residue at position 32 (corresponding to position 44 of hAM(1-52)) of the amino acid sequence of SEQ ID NO: 3 is substituted with glycine (Gly)), being amidated at the C-terminus thereof, and having a disulfide bond formed by cysteine residues at positions 4 (corresponding to position 16 of hAM(1-52)) and 9 (corresponding to position 21 of hAM(1-52)) is described as [Gly-44]hAM(13-52). A peptide consisting of an amino acid sequence of SEQ ID NO: 8 (i.e., an amino acid sequence such that arginine residue at position 32 (corresponding to position 44 of hAM(1-52)) of the amino acid sequence of SEQ ID NO: 3 is deleted), being amidated at the C-terminus thereof, and having a disulfide bond formed by cysteine residues at positions 4 (corresponding to position 16 of hAM(1-52)) and 9 (corresponding to position 21 of hAM (1-52)) is described as [des-Arg-44]hAM(13-52). A peptide consisting of an amino acid sequence of SEQ ID NO: 9 (i.e., an amino acid sequence such that arginine residue at position 32 (corresponding to position 44 of hAM(1-52)) of the amino acid sequence of SEQ ID NO: 3 is substituted with L-aspartic acid (Asp)), being amidated at the C-terminus thereof, and having a disulfide bond formed by cysteine residues at positions 4 (corresponding to position 16 of hAM(1-52)) and 9 (corresponding to position 21 of hAM (1-52)) is described as [Asp-44]hAM(13-52). A peptide consisting of an amino acid sequence of SEQ ID NO: 10 (i.e., an amino acid sequence such that arginine residue at position 32 (corresponding to position 44 of hAM(1-52)) of the amino acid sequence of SEQ ID NO: 3 is substituted with L-phenylalanine (Phe)), being amidated at the C-terminus thereof, and having a disulfide bond formed by cysteine residues at positions 4 (corresponding to position 16 of hAM(1-52)) and 9 (corresponding to position 21 of hAM(1-52)) is described as [Phe-44]hAM(13-52). A peptide consisting of an amino acid sequence of SEQ ID NO: 11 (i.e., an amino acid sequence such that serine residue at position 33 (corresponding to position 45 of hAM(1-52)) of the amino acid sequence of SEQ ID NO: 3 is substituted with proline (Pro)), being amidated at the C-terminus thereof, and having a disulfide bond formed by cysteine residues at positions 4 (corresponding to position 16 of hAM(1-52)) and 9 (corresponding to position 21 of hAM (1-52)) is described as [Pro-45]hAM(13-52). The compound according to the embodiment has a cyclic structure and C-terminal amide structure essential for the adrenomedullin activity, and has an amino acid sequence differing from that of natural human AM. Accordingly, the compound according to the embodiment having the properties can exhibit significantly superior pharmacokinetics, for example, with respect to biological stability, to the parent compound AM while maintaining pharmacological effects substantially equivalent to those of AM.

```
[D-Arg-44]hAM(13-52)
              (SEQ ID NO: 4, "*R" denotes D-arginine)
S-F-G-C-R-F-G-T-C-T-V-Q-K-L-A-H-Q-I-Y-Q-F-T-D-K-D-

K-D-N-V-A-P-*R-S-K-I-S-P-Q-G-Y-CONH2

[Lys-44]hAM(13-52)
                                        (SEQ ID NO: 5)
S-F-G-C-R-F-G-T-C-T-V-Q-K-L-A-H-Q-I-Y-Q-F-T-D-K-D-

K-D-N-V-A-P-K-S-K-I-S-P-Q-G-Y-CONH2

[Ala-44]hAM(13-52)
                                        (SEQ ID NO: 6)
S-F-G-C-R-F-G-T-C-T-V-Q-K-L-A-H-Q-I-Y-Q-F-T-D-K-D-

K-D-N-V-A-P-A-S-K-I-S-P-Q-G-Y-CONH2

[Gly-44]hAM(13-52)
                                        (SEQ ID NO: 7)
S-F-G-C-R-F-G-T-C-T-V-Q-K-L-A-H-Q-I-Y-Q-F-T-D-K-D-

K-D-N-V-A-P-G-S-K-I-S-P-Q-G-Y-CONH2

[des-Arg-44]hAM(13-52)
                                        (SEQ ID NO: 8)
S-F-G-C-R-F-G-T-C-T-V-Q-K-L-A-H-Q-I-Y-Q-F-T-D-K-D-

K-D-N-V-A-P-S-K-I-S-P-Q-G-Y-CONH2
```

-continued

[Asp-44]hAM(13-52)

(SEQ ID NO: 9)

S-F-G-C-R-F-G-T-C-T-V-Q-K-L-A-H-Q-I-Y-Q-F-T-D-K-D-

K-D-N-V-A-P-D-S-K-I-S-P-Q-G-Y-CONH₂

[Phe-44]hAM(13-52)

(SEQ ID NO: 10)

S-F-G-C-R-F-G-T-C-T-V-Q-K-L-A-H-Q-I-Y-Q-F-T-D-K-D-

K-D-N-V-A-P-F-S-K-I-S-P-Q-G-Y-CONH₂

[Pro-45]hAM(13-52)

(SEQ ID NO: 11)

S-F-G-C-R-F-G-T-C-T-V-Q-K-L-A-H-Q-I-Y-Q-F-T-D-K-D-

K-D-N-V-A-P-R-P-K-I-S-P-Q-G-Y-CONH₂

In the compound according to the aspect, the peptide is particularly preferably a peptide consisting of an amino acid sequence of any of SEQ ID NOs: 4 to 11, being amidated at the C-terminus thereof, and having a disulfide bond formed by cysteine residues at positions 4 and 9. Accordingly, the compound according to the aspect having the properties can exhibit significantly superior pharmacokinetics, for example, with respect to biological stability, to the parent compound AM while maintaining pharmacological effects substantially equivalent to those of AM.

In the present specification, "C-terminal amidation" means an aspect of post-translational modification of a peptide in a living body, and specifically means a reaction in which the main chain carboxyl group of C-terminal amino acid residue of the peptide is converted into an amide group. In the present specification, "formation of a disulfide bond between cysteine residues" or "disulfide bond formation by cysteine residues" means an aspect of post-translational modification of a peptide in a living body, and specifically means a reaction in which two cysteine residues in an amino acid sequence of a peptide form a disulfide bond (—S—S—). Many bioactive peptides produced in a living body are initially biosynthesized as a precursor protein with larger molecular weight. The precursor protein is subject to post-translational modifications, such as C-terminal amidation and/or disulfide bond formation by cysteine residues, during a process of intracellular transport to give a mature bioactive peptide. The C-terminal amidation typically proceeds by a C-terminal amidating enzyme that acts on a precursor protein. For a bioactive peptide having a C-terminal amide group, the precursor protein has a Gly residue bound to a C-terminal carboxyl group to be amidated and the Gly residue is converted into a C-terminal amide group by the C-terminal amidating enzyme. The C-terminal propeptide in the precursor protein has a repeat sequence comprising a combination of basic amino acid residues, such as Lys-Arg or Arg-Arg (Mizuno, Journal of Japanese Biochemical Society, 61 (12): 1435-1461 (1989)). Disulfide bond formation by cysteine residues can proceed under oxidative conditions. Disulfide bond formation by cysteine residues in a living body typically proceeds by a protein disulfide isomerase that acts on the precursor protein.

The peptide of (b) can be formed by oxidizing thiol groups of two cysteine residues in the peptide of (a) with air or with a suitable oxidizing agent to form a disulfide bond. The peptide of (b) can be used to establish a conformation of the compound according to the aspect similar to that of natural AM. This similar conformation can lead adrenomedullin activity of the compound according to the aspect to an activity substantially approximately equivalent to that of natural AM.

The peptide of (c) can be formed by converting a disulfide bond in the peptide of (b) into an ethylene group. The substitution of a disulfide bond to an ethylene group can be accomplished by any method well known in the art (O. Keller et al., Helv. Chim. Acta, 1974, Volume 57, p. 1253). The peptide of (c) can be used to stabilize a conformation of the compound according to the aspect. Thereby, the compound according to the aspect can exhibit significantly superior pharmacokinetics, for example, with respect to biological stability, to the parent compound AM while maintaining pharmacological effects substantially equivalent to those of AM.

In the peptide of (d), the number of amino acid residues deleted or added preferably ranges from 1 to 3, is more preferably 1 or 2, and further preferably 1. However, each of the deleted amino acid residues is neither the cysteine residue at position 4 nor that at position 9. Each of the deleted amino acid residues is preferably not the substituted amino acid residue in the peptide of (a). In the embodiment, a suitable peptide of (d) is a peptide wherein amino acid residues in the specified number among the amino acid residues at positions 1 to 3 and 10 to 40 of any peptide of (a) to (c) are deleted or added (preferably added), and a more suitable peptide of (d) is a peptide wherein amino acid residues in the specified number among the amino acid residues at positions 1 to 3 and 29 to 35 of any peptide of (a) to (c) are deleted or added (preferably added). The suitable peptide may have further deletion or addition of one or more (such as 1 to 3, or 1 or 2) amino acid residues. The peptide of (d) can be used to achieve adrenomedullin activity of the compound according to the embodiment substantially approximately equivalent to that of natural AM. Also, the peptide of (d) can be used to allow the compound according to the embodiment to exhibit significantly superior pharmacokinetics, for example, with respect to biological stability, to the parent compound AM while maintaining pharmacological effects substantially equivalent to those of AM.

The peptide of (f) can be converted to the peptide of (e) by a C-terminal amidating enzyme which can convert a glycine residue at the C-terminus of the peptide of (f) into a C-terminal amide group. Therefore, the peptide of (f) can be administered to a subject to form the peptide of (e) amidated at the C-terminus thereof in a living body of the subject after a certain period of time. Thus, the compound according to the aspect can sustainably exert adrenomedullin activity in a living body.

The peptides of (a) to (f) shown above as examples exert adrenomedullin activity in normal cases. The compound according to the embodiment, being any of the peptides of (a) to (f) that has the properties and exerts adrenomedullin activity, can exhibit significantly superior pharmacokinetics, for example, with respect to biological stability, to the parent compound AM while maintaining pharmacological effects substantially equivalent to those of AM.

In each aspect of the invention, "adrenomedullin activity" means various physiological effects, for example, shown as examples in the following.

(1) Cardiovascular: a vasodilatory effect, an effect of lowering blood pressure, an effect of suppressing increase in blood pressure, an effect of increasing cardiac output or improving cardiac insufficiency, an effect of improving pulmonary hypertension, an angiogenic effect, a lymphangiogenic effect, an effect of improving vascular endothelial function, control of vasopermeability, control of endothelial intercellular adhesion, an endothelial barrier protection effect, an antiarteriosclerotic effect, a myocardial protective effect (such as a myocardial protective effect in ischemic reperfusion disorder or inflammation), an effect of suppressing postmyocardial remodeling, an effect of suppressing cardiac hypertrophy, and an effect of suppressing an angiotensin-converting enzyme.

(2) Kidney and water and electrolyte system: a diuretic effect, a natriuretic effect, an effect of suppressing antidiuretic hormone, an aldosterone-reducing effect, a renoprotective effect (such as a myocardial protective effect in high blood pressure or ischemic reperfusion disorder), an effect of suppressing diabetic renal disease, an effect of suppressing C3 nephropathy, an effect of suppressing drinking behavior, and an effect of suppressing salt requirement.

(3) Brain and nervous system: an effect of neuroprotection and suppressing encephalopathy, an anti-inflammatory effect, an effect of suppressing apoptosis (such as an effect of suppressing apoptosis in ischemic reperfusion disorder or inflammation), an effect of maintaining autoregulatory capacity, an effect of suppressing oxidative stress, an effect of improving dementia, and a sympathoinhibitory effect.

(4) Urogenital: an effect of improving erection, an effect of improving blood flow, and an implantation-promoting effect.

(5) Gastrointestinal system: an antiulcer effect, a tissue repair effect, an effect of neogenesis of mucous membrane, an intestinal barrier protection effect, an effect of improving blood flow, an anti-inflammatory effect, and an effect of improving liver function.

(6) Orthopedics: an effect of stimulating osteoblast and an effect of improving arthritis.

(7) Endocrine metabolic system: an adipocyte-differentiating effect, an effect of regulating lipolysis, an effect of improving insulin sensitivity, an effect of controlling insulin secretion, an effect of suppressing antidiuretic hormone secretion, and an effect of suppressing aldosterone secretion.

(8) Respiratory system: a bronchodilating effect, a lung protection effect, an effect of improving emphysema, suppression of pulmonary fibrogenesis, suppression of pneumonia, an effect of suppressing bronchitis, and an effect of improving respiration.

(9) Immune system: an effect of promoting decomposition of C3b.

(10) Other: an antiviral effect, an effect of improving circulation, an anti-inflammatory effect, an effect of modulating cytokine, an organ protective effect, an effect of suppressing oxidative stress, a tissue repair effect (such as an anti-decubitus effect), an effect of improving septicemia, an effect of improving septic shock, an effect of suppressing multiple organ failure, an effect of suppressing auto-immune disease, an effect of suppressing diabetic retinopathy, an antimicrobial effect, a hair growth effect, and a pilatory effect.

The blood pressure-lowering effect is preferably a vasodilatory hypotensive effect. The anti-inflammatory effect in the gastrointestinal system is preferably an effect of preventing or treating inflammatory bowel diseases including a steroid-resistant or steroid-dependent inflammatory bowel disease (such as ulcerative colitis, Crohn's disease, or intestinal tract Behcet's disease).

The adrenomedullin activity exerted by AM, shown above with examples, will be exerted via increased concentration of intracellular cAMP in normal cases. Thus, the increased concentration of intracellular cAMP can be considered as an index of the adrenomedullin activity of the compound according to the aspect. In each aspect of the invention, the effect of increasing concentration of intracellular cAMP can be evaluated, for example, by adding a target compound to a cultured cell line (HEK293 cell line) caused to stably express an AM type 1 receptor (AMI receptor) and measuring the amount of intracellular cAMP produced. The compound according to the aspect has the effect of increasing concentration of intracellular cAMP substantially approximately equivalent to that of natural AM. Accordingly, the compound according to the aspect can exert bioactivity substantially approximately equivalent to that of natural AM (i.e., adrenomedullin activity) via increased concentration of intracellular cAMP.

In each aspect of the invention, the compound according to the aspect includes not only the compound itself but also a salt thereof. When the compound according to the aspect is in the form of salt, it is preferably a pharmaceutically acceptable salt. Counterions in a salt of the compound according to the aspect preferably include, but are not limited to, for example, cations such as a sodium, potassium, calcium, magnesium, or substituted or unsubstituted ammonium ion, or anions such as a chloride, bromide, iodide, phosphate, nitrate, sulfate, carbonate, bicarbonate, perchlorate, formate, acetate, trifluoroacetate, propionate, lactate, maleate, hydroxymaleate, methylmaleate, fumarate, adipate, benzoate, 2-acetoxy benzoate, p-aminobenzoate, nicotinate, cinnamate, ascorbate, pamoate, succinate, salicylate, bismethylenesalicylate, oxalate, tartrate, malate, citrate, gluconate, aspartate, stearate, palmitate, itaconate, glycolate, glutamate, benzenesulfonate, cyclohexylsulfamate, methanesulfonate, ethanesulfonate, isethionate, benzenesulfonate, p-toluenesulfonate, or naphthalenesulfonate ion. When the compound according to the aspect is in the form of salt with any of the counterions, adrenomedullin activity of the compounds can be substantially approximately equivalent to that of natural AM.

In each aspect of the invention, the compound according to the aspect includes not only the compound itself but also a solvate of the compound or a salt thereof. When the compound according to the aspect or a salt thereof is in the form of a solvate, it is preferably a pharmaceutically acceptable solvate. Solvents that can form solvates with the compound or a salt thereof preferably include, but are not limited to, for example, water or organic solvents such as methanol, ethanol, 2-propanol (isopropyl alcohol), dimethyl sulfoxide (DMSO), acetic acid, ethanolamine, acetonitrile, or ethyl acetate. When the compound according to the aspect or a salt thereof is in the form of solvate with any of the solvents described above, adrenomedullin activity of the compounds can be substantially approximately equivalent to that of AM.

In each aspect of the invention, the compound according to the aspect includes not only the compound itself but also a derivative thereof. Derivatives of the compound according to the aspect when the compound according to the aspect is in the form of derivative include, but are not limited to, for example, compounds having a modifying group and/or linking group disclosed in International Publication Nos. WO 2015/141819, WO 2017/047788, WO 2018/181638, and so forth. Those skilled in the art could prepare such a compound by derivatizing the compound according to the aspect with reference to any of the literatures. The AM derivatives disclosed in the literatures can exert pharmacological effects of adrenomedullin without substantially causing unwanted side effects. Accordingly, when the compound according to the aspect is in the form of any of the derivatives, the compound can exhibit significantly superior pharmacokinetics, for example, with respect to biological stability, to AM while substantially avoiding the occurrence of unwanted side effects.

In each aspect of the invention, the compound according to the aspect includes not only the compound itself described above or below but also a protected form thereof. In the present specification, a "protected form" means a form in which any protecting group is introduced into one or more functional groups (such as a side-chain amino group of lysine residue) of the compound. In the present specification, a "protecting group" means a group that is introduced into a specific functional group to prevent any unwanted reaction from proceeding, will be removed quantitatively under a specific reaction condition, and is substantially stable, or inactive, under any reaction condition other than the specific reaction condition. Protecting groups that can form protected forms of the compounds include, but are not limited to, for example, t-butoxycarbonyl (Boc), 2-bromobenzyloxycarbonyl (BrZ), 9-fluorenylmethoxycarbonyl (Fmoc), p-toluenesulfonyl (Tos), benzyl (Bzl), 4-methylbenzyl (4-MeBzl), 2-chlorobenzyloxycarbonyl (ClZ), cyclohexyl (cHex), and phenacyl (Pac); other protecting groups of amino groups include benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenyl) isopropyloxycarbonyl, 2-(3,5-dimethoxyphenyl) isopropyloxycarbonyl, p-phenylazobenzyloxycarbonyl, triphenylphosphonoethyloxycarbonyl, 9-fluorenylmethyloxycarbonyl, t-amyloxyoxycarbonyl, diisopropylmethyloxycarbonyl, isopropyloxycarbonyl, ethyloxycarbonyl, allyloxycarbonyl, 2-methylsulfonylethyloxycarbonyl, 2,2,2-trichloroethyloxycarbonyl, cyclopentyloxycarbonyl, cyclohexyloxycarbonyl, adamantyloxycarbonyl, isobornyloxycarbonyl, benzenesulfonyl, mesitylenesulfonyl, methoxytrimethylphenylsulfonyl, 2-nitrobenzenesulfonyl, 2-nitrobenzenesulfenyl, 4-nitrobenzenesulfonyl, and 4-nitrobenzenesulfenyl: other protecting groups of carboxyl groups include methyl esters, ethyl esters, t-butyl esters, p-methoxy benzyl esters, and p-nitrobenzyl esters: other side-chain protecting groups of Arg include 2,2,4,6,7-pentamethyl-2,3-dihydrobenzofuran-5-sulfonyl, 4-methoxy-2,3,6-trimethylbenzenesulphonyl, 2,2,5,7,8-pentamethylchroman-6-sulfonyl, and 2-methoxybenzenesulfonyl: other protecting groups of Tyr include 2,6-dichlorobenzyl, t-butyl, and cyclohexyl: other protecting groups of Cys include 4-methoxy benzyl, t-butyl, trityl, acetamidomethyl, and 3-nitro-2-pyridine sulfenyl: other protecting groups of His include benzyloxymethyl, p-methoxybenzyloxymethyl, t-butoxymethyl, trityl, and 2,4-dinitrophenyl; and other protecting groups of Ser and Thr include t-butyl. When the compound according to the aspect is in a protected form with any of the protecting groups described above, adrenomedullin activity of the compound may be substantially approximately equivalent to that of natural AM.

In each aspect of the invention, the compound according to the aspect includes individual enantiomer and diastereomer of the compounds, and mixtures of stereoisomeric forms of the compounds such as racemates.

The compound according to the aspect having the properties can exhibit significantly superior pharmacokinetics, for example, with respect to biological stability, to the parent compound AM while maintaining pharmacological effects substantially equivalent to those of AM.

<2. Pharmaceutical Use of Adrenomedullin Analog>

A compound according to an aspect of the invention can exhibit significantly superior pharmacokinetics to the parent compound AM while maintaining pharmacological effects substantially equivalent to those of AM. Therefore, another aspect of the invention relates to a medicament comprising a compound according to an aspect of the invention as an active ingredient.

A compound according to an aspect of the invention may be used alone or in combination with one or more pharmaceutically acceptable components when the compound is applied to pharmaceutical use. A medicament according to the aspect can be formulated into various dosage forms commonly used in the art depending on the desired mode of administration. Thus, the medicament according to the aspect can also be provided in the form of a pharmaceutical composition comprising a compound according to an aspect of the invention or a pharmaceutically acceptable salt thereof, or a pharmaceutically acceptable solvate thereof, and one or more pharmaceutically acceptable carriers. In the case of the embodiment, pharmaceutical compositions may comprise, in addition to the components described above, one or more pharmaceutically acceptable media (e.g., solvent such as sterile water or solution such as physiological saline) and additive agents including excipients, binders, vehicles, dissolution aids, preservatives, stabilizers, disintegrators, disintegration inhibitors, bulking agents, lubricants, surfactants, emulsifying agents, oily liquids (such as plant oil), suspending agents, buffering agents, soothing agents, antioxidants, sweetening agents, flavoring agents, and so forth.

The dosage form of the medicament according to the aspect is not particularly limited and may be a formulation for parenteral administration, a formulation for transmucosal (such as transnasal, sublingual, or trans-oral-mucosal), transdermal, transanal (intestinal infusion), or transvaginal administration, or a formulation for oral administration. The dosage form of the medicament according to the aspect may also be a formulation in unit dosage form or in multiple dosage form. Formulations for use in parenteral administration include, for example, injections such as sterile solutions or suspensions in water or any other pharmaceutically acceptable liquid. Additive agents that can be admixed into the injections include, but are not limited to, for example, vehicles such as physiological saline and isotonic solutions comprising glucose or other pharmaceutic aids (such as D-sorbitol, D-mannitol, or sodium chloride); dissolution aids such as alcohols (such as ethanol or benzyl alcohol), esters (such as benzyl benzoate), and polyalcohols (such as propylene glycol or polyethylene glycol); nonionic surfactants such as polysorbate 80 or polyoxyethylene hydrogenated castor oil; oily liquids such as sesame oil or soybean oil; buffering agents such as phosphate buffer or sodium acetate buffer; soothing agents such as benzalkonium chloride or procaine hydrochloride; stabilizers such as human serum albumin or polyethylene glycol; preservatives; and antioxidants. The prepared injection will be generally filled in any suitable container (such as a vial or an ampule) and preserved under an appropriate environment until use.

Additive agents to be comprised in formulations for use in transmucosal administration include, for example, media, emulsifying agents, suspending agents, antibacterial agents (such as chlorobutanol), isotonic agents (such as sodium chloride), pH adjusters, and penetrating agents. Additive agents to be comprised in formulations for use in transdermal administration include, for example, media, antipruritic agents, antifoaming agents, emollients, surfactants, emulsifying agents, thickeners, suspending agents, buffering agents, viscosity enhancers, moisturizers, antioxidants, chemical stabilizers, coloring agents, and decolorizing agents. Additive agents to be comprised in formulations for use in transanal administration include, for example, media, emulsifying agents, and solid fat bases. Additives to be comprised in formulations for use in transvaginal administration include, for example, media, buffering agent, oily liquids, suspending agents, wetting agents, surfactants, antioxidants, antibacterial agents, and isotonic agents.

The formulations for use in oral administration include, for example, a tablet, a pill, a powder, a capsule, a soft capsule, a microcapsule, an elixir, a liquid, a syrup, a slurry, and a suspension. A tablet may be formulated as a dosage form of a sugar-coated tablet coated with sugar coating or soluble film, a gelatin-encapsulated tablet, an enteric-coated tablet, an orally disintegrating tablet (OD tablet), or a film-coated tablet, or formulated as a dosage form of a double-coated tablet or a multi-coated tablet.

Additive agents that can be admixed into tablets or capsules and so forth include, but are not limited to, for example, binders such as water, ethanol, propanol, simple syrup, glucose solution, carboxymethylcellulose, shellac, methylcellulose, potassium phosphate, polyvinylpyrrolidone, gelatin, cornstarch, gum tragacanth, and gum arabic; excipients such as crystalline cellulose, lactose, white soft sugar, sodium chloride, glucose, urea, starch, calcium carbonate, kaolin, or silicic acid; disintegrators such as dry starch, sodium arginate, agar powder, laminaran powder, sodium bicarbonate, calcium carbonate, polyoxyethylene sorbitan fatty acid ester, sodium laurylsulfate, stearic acid monoglyceride, starch, lactose, or polyvinylpyrrolidone; disintegration inhibitors such as white soft sugar, stearin, cacao butter, or hydrogenated oil; bulking agents such as cornstarch, gelatin, or alginate; lubricants such as magnesium stearate; absorption accelerators such as quaternary ammonium salts or sodium laurylsulfate; wetting agents such as glycerin or starch; adsorbents such as starch, lactose, kaolin, bentonite, or colloidal silicic acid; lubricants such as purified talc, stearates (such as magnesium stearate), boric acid powder, or polyethylene glycol; sweetening agents such as sucrose, lactose, or saccharin; and flavoring agents such as peppermint, Gaultheria adenothrix oil, or cherry. A formulation may further include liquid carriers such as oils/fats when the formulation is in the form of a capsule.

The medicament according to the aspect can be formulated into a depot formulation. In this case, the medicament according to the aspect in the dosage form of depot formulation can, for example, be implanted subcutaneously or intramuscularly or administered by intramuscular injection. The depot formulation of the medicament according to the aspect allows a compound according to an aspect of the invention to sustainably exert adrenomedullin activity for a long period of time.

As described hereinbefore, a compound according to an aspect of the invention exhibits significantly superior pharmacokinetics, for example, with respect to biological stability, to the parent compound AM while maintaining pharmacological effects substantially equivalent to those of AM. Therefore, the medicament according to the aspect is preferably formulated as a formulation in the form of single administration, and more preferably formulated as a formulation in the form of single subcutaneous administration.

The medicament according to the aspect can be combined with one or more other drugs useful as medicaments. In this case, the medicament according to the aspect may be provided in the form of a single medicament comprising a compound according to an aspect of the present invention or a pharmaceutically acceptable salt thereof, or a pharmaceutically acceptable solvate thereof, and one or more other drugs, or may be provided in the form of a medicament combination or kit comprising a plurality of formulations into which a compound according to an aspect of the present invention or a pharmaceutically acceptable salt thereof, or a pharmaceutically acceptable solvate thereof, and one or more other drugs are separately formulated. For the medicament combination or kit, each formulation can be administered simultaneously or separately (such as sequentially).

For applying a compound according to an aspect of the invention to pharmaceutical use, the compound according to an aspect of the invention includes not only the compound itself but also a pharmaceutically acceptable salt thereof and a pharmaceutically acceptable solvate thereof. The pharmaceutically acceptable salts of a compound according to an aspect of the invention and pharmaceutically acceptable solvates thereof preferably include, but are not limited to, for example, salts or solvates exemplified above. When a compound according to an aspect of the invention is in the form of any of the salts or solvates described above, the compound can be applied to the desired pharmaceutical use.

The medicament according to the aspect comprising a compound according to an aspect of the invention or a pharmaceutically acceptable salt thereof, or a pharmaceutically acceptable solvate thereof as an active ingredient can prevent or treat various conditions, diseases, and/or disorders that will be prevented or treated with AM. The conditions, diseases, and/or disorders include, but are not limited to, for example, the following:

(1) Cardiovascular diseases: cardiac insufficiency, pulmonary hypertension, arteriosclerosis obliterans, Buerger's disease, myocardial infarction, lymphedema, Kawasaki's disease, myocarditis, cardiac arrhythmia (such as cardiac arrhythmia after catheter ablation surgery), atrial fibrillation, aortitis, pulmonary hypertension, high blood pressure, organ dysfunctions due to high blood pressure, peripheral vascular diseases, and arteriosclerosis.

(2) Kidney and water and electrolyte system diseases: kidney failure and nephritis.

(3) Brain and nervous system diseases: cerebral infarction, dementia, vascular dementia, Alzheimer's disease, and encephalitis.

(4) Urogenital diseases: erectile dysfunction (ED).

(5) Gastrointestinal diseases: inflammatory diseases (such as inflammatory bowel disease or Crohn's disease), ulcerative diseases (such as ulcerative colitis), intestinal tract Behcet's disease, hepatitis, hepatic fibrosis, cirrhosis, and hepatic failure.

(6) Orthopedic disease: arthritis.

(7) Endocrine metabolic disease: diabetes and organ dysfunctions due to diabetes (such as diabetic renal disease or diabetic retinopathy), and primary aldosteronism.

(8) Respiratory diseases: bronchial asthma, emphysema, pulmonary fibrosis, pneumonia, acute bronchitis, chronic bronchitis, and acute respiratory distress syndrome (ARDS).

(9) Immune diseases: diseases associated with the complement system (such as C3 nephropathy).

(10) Other diseases: viral infections, septicemia, septic shock, auto-immune disease, multiple organ failure, pressure sore, wound healing, and alopecia.

The cardiovascular disease that will be prevented or treated with the medicament according to the aspect is, in particular, cardiac insufficiency, myocardial infarction (such as acute myocardial infarction), cardiac arrhythmia (such as cardiac arrhythmia after catheter ablation surgery), atrial fibrillation, pulmonary hypertension, or peripheral vascular diseases. The brain and nervous system disease that will be prevented or treated with the medicament according to the aspect is, in particular, cerebral infarction or dementia. The gastrointestinal disease that will be prevented or treated with the medicament according to the aspect is, in particular, an inflammatory disease (such as inflammatory bowel disease or Crohn's disease), an ulcerative disease (such as ulcerative colitis), or intestinal tract Behcet's disease. The endocrine metabolic disease that will be prevented or treated with the medicament according to the aspect is, in particular, diabetes and organ dysfunctions due to diabetes (such as diabetic renal disease or diabetic retinopathy). The respiratory disease that will be prevented or treated with the medicament according to the aspect is, in particular, pulmonary fibrosis. Another disease that will be prevented or treated with the medicament according to the aspect is, in particular, septicemia, septic shock, or a viral infection.

Viruses that cause a viral infection for the medicament according to the aspect include, for example, one or more viruses selected from the group consisting of influenzavirus, novel coronavirus (SARS-COV-2), severe acute respiratory syndrome (hereinafter also described as "SARS") coronavirus, Middle East respiratory syndrome (hereinafter also described as "MERS") coronavirus, conventional human coronavirus (229E, NL63, OC43, and HKU1), RS virus, adenovirus, varicella-zoster virus, herpes simplex virus, measles virus, parainfluenza virus, enterovirus, rhinovirus, and human metapneumovirus, and, in particular, include one or more viruses selected from the group consisting of influenzavirus and SARS-COV-2. Examples of viral infections caused by the viruses shown as examples include, but are not limited to, for example, viral pneumonia, viral myocarditis, viral encephalitis, viral hemorrhagic fever, viral nephropathy, viral gastroenteritis, viral vasculitis, viral stomatitis, viral keratitis, and viral neuritis, in particular, viral pneumonia.

The medicament according to the aspect is preferably a medicament for use in the prevention or treatment of the condition, disease, and/or disorder described above (such as a cardiovascular disease, a brain and nervous system disease, or a gastrointestinal disease), and more preferably a medicament for use in the prevention or treatment of cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection. The medicament according to the aspect can be used to prevent or treat the condition, disease, and/or disorder described above to exert preventive or therapeutic effects substantially equivalent to those of AM with significantly superior pharmacokinetics to AM.

In the present specification, "prevention" means that onset (development or occurrence) of a condition, disease, and/or disorder will be substantially precluded. On the other hand, in the present specification, "treatment" means suppression (such as suppression of progression), remission, restoration, and/or cure of a condition, disease, and/or disorder that has appeared (developed or occurred).

A compound according to an aspect of the invention is an analog peptide of AM, which is a natural bioactive peptide. This allows the compound according to an aspect of the invention to be safe and have low toxicity. Therefore, the medicament according to the aspect comprising the compound according to an aspect of the invention or a pharmaceutically acceptable salt thereof, or a pharmaceutically acceptable solvate as an active ingredient can be applied to various subjects in need of prevention or treatment of the condition, disease, and/or disorder. The subjects are preferably human or non-human mammalian (such as warm-blooded animal including pig, dog, cattle, rat, mouse, guinea pig, rabbit, chicken, sheep, cat, monkey, hamadryas baboon, or chimpanzee) subjects or patients, and more preferably human patients. The medicament according to the aspect can be administered to the subjects to prevent or treat the condition, disease, and/or disorder in the subjects.

When the medicament according to the aspect is administered to a subject, particularly a human patient, the precise dosage and administration will be determined considering many factors including age and sex of the subject, the precise condition (such as severity) of the condition, disease, and/or disorder to be prevented or treated, and the route of administration. The therapeutically effective dosage and administration should be ultimately determined by the attending physician. Therefore, the compound according to an aspect of the invention or a pharmaceutically acceptable salt, or a pharmaceutically acceptable solvate thereof, which is an active ingredient in the medicament according to the aspect, will be administered to the subject in the therapeutically effective dosage and administration (such as dose, number of doses, and route of administration). For example, when the medicament according to the aspect is administered to a human patient, a dose of the compound according to an aspect of the invention or a pharmaceutically acceptable salt, or a pharmaceutically acceptable solvate thereof, which is used as an active ingredient, will usually range from 0.01 to 1000 µg/kg body weight/day, for example, range from 0.5 to 200 µg/kg body weight/day.

The medicament according to the present aspect may be administered in any number of doses through any route of administration. As described hereinbefore, a compound according to an aspect of the invention exhibits significantly superior pharmacokinetics, for example, with respect to biological stability, to the parent compound AM while maintaining pharmacological effects substantially equivalent to those of AM. Therefore, the medicament according to the aspect is preferably administered in a single dose. The medicament according to the aspect is preferably administered parenterally such as intravenously, by intestinal infusion, subcutaneously, intramuscularly, or intraperitoneally, and more preferably subcutaneously. The medicament according to the aspect comprising AM or an adrenomedullin derivative as an active ingredient can be used with the dosage and administration (such as dose, number of doses, and route of administration) to prevent or treat the condition, disease, and/or disorder in subjects.

Likewise, a compound according to an aspect of the invention can prevent or treat the above-described conditions, diseases, and/or disorders that will be prevented or treated with AM. Therefore, another aspect of the invention relates to an agent for preventing or treating the conditions, diseases, and/or disorders described above, the agent comprising a compound according to an aspect of the invention or a pharmaceutically acceptable salt thereof, or a pharmaceutically acceptable solvate thereof as an active ingredient. The agent for prevention or treatment according to an aspect of the invention has the same properties as the above-described medicament according to the aspect. The agent for prevention or treatment according to the aspect can be used for the same conditions, diseases, and/or disorders with the same dosage and administration as for the above-described medicament according to the aspect.

The compound according to an aspect of the invention can be used for the prevention or treatment of the condition, disease, and/or disorder described above in a patient having the condition, disease, and/or disorder. Therefore, another aspect of the invention is a method for preventing or treating the condition, disease, and/or disorder described above, comprising administering an effective amount of the compound according to an aspect of the invention or a pharmaceutically acceptable salt thereof, or a pharmaceutically acceptable solvate thereof to a subject in need of prevention or treatment of the condition, disease, and/or disorder. In the method according to the aspect, the compound according to an aspect of the invention or the like can be administered to a subject with the same dosage and administration as for the above-described medicament according to the aspect. The condition, disease, and/or disorder are preferably any of cardiovascular diseases, brain and nervous system diseases, gastrointestinal diseases, endocrine metabolic diseases, respiratory diseases, and other diseases, and more preferably any of cardiac insufficiency, acute myocardial infarction, cardiac arrhythmia, atrial fibrillation, pulmonary hypertension, peripheral vascular diseases, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, and viral infections. An effective amount of the compound according to an aspect of the invention or a pharmaceutically acceptable salt thereof, or a pharmaceutically acceptable solvate thereof can be administered to subjects in need of prevention or treatment of the condition, disease, and/or disorder to prevent or treat the condition, disease, and/or disorder.

Another aspect of the invention is a compound according to an aspect of the invention or a pharmaceutically acceptable salt, or a pharmaceutically acceptable solvate thereof for use in the prevention or treatment of the condition, disease, and/or disorder described above. Yet another aspect of the invention is use of a compound according to an aspect of the invention or a pharmaceutically acceptable salt, or a pharmaceutically acceptable solvate thereof in the manufacture of a medicament for the prevention or treatment of the condition, disease, and/or disorder described above. Yet another aspect of the invention is use of a compound according to an aspect of the invention or a pharmaceutically acceptable salt, or a pharmaceutically acceptable solvate thereof for the prevention or treatment of the condition, disease, and/or disorder described above. The compound according to an aspect of the invention or the like can be used for administering to a subject with the same dosage and administration as for the above-described medicament according to the aspect. The condition, disease, and/or disorder are preferably any of cardiovascular diseases, brain and nervous system diseases, gastrointestinal diseases, endocrine metabolic diseases, respiratory diseases, and other diseases, and more preferably any of cardiac insufficiency, acute myocardial infarction, cardiac arrhythmia, atrial fibrillation, pulmonary hypertension, peripheral vascular diseases, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, and viral infections. The compound according to an aspect of the invention or a pharmaceutically acceptable salt thereof, or a pharmaceutically acceptable solvate thereof can be used for the prevention or treatment of the condition, disease, and/or disorder described above to prevent or treat the condition, disease, and/or disorder.

<3. Method for Producing Adrenomedullin Analog>

Yet another aspect of the invention relates to a method for producing a compound according to an aspect of the invention.

The compound according to an aspect of the invention has a polypeptide structure as a whole. Therefore, the compound according to an aspect of the invention can be produced on the basis of various means, such as synthetic means or cultural means, which are used in the art for synthesizing polypeptides.

For example, in the case of producing a compound according to an aspect of the invention on the basis of synthetic means, a peptide chain having the amino acid sequence of the compound according to an aspect of the invention can be synthesized by peptide synthesis on solid phase system or in liquid phase system. Therefore, the method according to the aspect based on the synthetic means comprises a peptide chain synthesis step of synthesizing a peptide chain having the amino acid sequence of the compound according to an aspect of the invention by peptide synthesis on solid phase system or in liquid phase system. A compound according to an aspect of the invention as the peptide of (a), (d), or (f) can be obtained by performing the step. The compound according to an aspect of the invention as the peptide of (e) can be obtained by using an amino acid having a C-terminal amide structure in advance as a raw material of the C-terminal amino acid residue in the step.

In the method according to the aspect based on the synthetic means, a compound according to an aspect of the invention as the peptide of (b), which has a disulfide bond formed by two cysteine residues in the amino acid sequence, can be obtained by disulfide bond formation between thiol groups of two cysteine residues in the amino acid sequence of the peptide chain obtained by the peptide chain synthesis step. Also, a compound according to an aspect of the invention as the peptide of (c), in which the disulfide bond formed between two cysteine residues in the amino acid sequence of the peptide chain obtained by the peptide chain synthesis step has been substituted with an ethylene group, can be obtained by substitution of the disulfide bond with an ethylene group. The formation reaction of a disulfide bond and the substitution reaction with an ethylene group can be performed based on any condition commonly used in the art.

When at least any of the peptide chain obtained by the peptide chain synthesis step and a precursor thereof are in a protected form in the method according to the aspect based on the synthetic means, the method according to the aspect may comprise a protection step in which one or more protecting groups are introduced into the peptide chain or the precursor thereof and/or a deprotection step in which at least any of one or more protecting groups in protected forms of the peptide chain or the precursor thereof are deprotected, as desired. The protection and deprotection steps can be performed with any protection and deprotection reaction commonly used in the art.

For example, in the case of producing a compound according to an aspect of the invention on the basis of cultural means, a host cell capable of producing the compound according to an aspect of the invention is prepared and subsequently allowed to overexpress the compound of interest. Therefore, the method according to the aspect based on the cultural means comprises an expression step of overexpressing the compound according to an aspect of the invention in a host cell capable of producing the compound.

The host cell capable of producing the compound according to an aspect of the invention can be obtained by obtaining an isolated nucleic acid having a nucleotide sequence encoding the compound according to an aspect of the invention, subsequently linking the nucleic acid to a vector, and introducing the resultant to cells such as *Escherichia coli* or *Saccharomyces cerevisiae* for transformation.

The method according to the aspect based on cultural means can be performed by applying means for gene recombination and gene expression commonly used in the art.

EXAMPLES

Hereinafter, the present invention will be described further specifically with reference to Examples. However, the technical scope of the present invention is not intended to be limited by these Examples.

Experiment I: Decomposition of AM in Plasma and Serum

[Decomposition Reaction of AM]

Used as AM was mature natural human adrenomedullin (hAM(1-52)), a peptide consisting of the amino acid sequence of SEQ ID NO: 1, being amidated at the C-terminus thereof, and having a disulfide bond formed by cysteine residues at positions 16 and 21. Prepared was a reaction mixture containing 10 mM $NaH_2PO_4$ buffer (pH 7.1), 10 mM NaCl, and 100 μl of serum or plasma in a final volume of 0.2 ml. hAM(1-52) was added to the reaction mixture, and reaction was initiated at 37° C. After the lapse of a predetermined time, a 30-μl portion was taken out of the reaction solution, transferred into 170 μl of 0.1% aqueous solution of trifluoroacetic acid (TFA), and stored at –80° C. until analysis.

[Quantitative Analysis of AM by Fluoroimmunoassay]

Quantitative analysis was performed for AM contained in the thus-obtained samples of a reaction mixture with serum or plasma by using specific fluoroimmunoassay (Tosoh Corporation) with two antibodies differing in their recognition sites. The first antibody binds to a cyclic structure having a disulfide bond formed by cysteine residues at positions 16 and 21 of hAM(1-52), and the second antibody binds to the C-terminal part of AM. Use of these two antibodies allows quantitative analysis of AM as mature AM (hAM(1-52)) that can exhibit activity (Ohta H et al., One-step direct assay for mature-type adrenomedullin with monoclonal antibodies. Clin Chem., February 1999, Volume 45, Issue 2, p. 244-51; Kubo K et al., Biological properties of adrenomedullin conjugated with polyethylene glycol. Peptides, July 2014, Volume 57, p. 118-21. doi: 10.1016/j.peptides.2014.05.005. Epub 2014 May 27.). FIG. 1 shows time course of concentration of AM contained in the samples of a rection mixture with serum or plasma. In the figure, the abscissa represents reaction time (min), and the ordinate represents concentration of AM (UM).

As shown in FIG. 1, the amount of the mature AM hAM(1-52) rapidly decreased with the lapse of reaction time in the reaction mixture with serum, and a concentration below the detection limit was reached 240 minutes after the beginning of reaction. On the other hand, hAM(1-52) was stable in the reaction mixture with plasma. For example, 85% to the amount of hAM(1-52) at the beginning of reaction was maintained in the reaction mixture with plasma even 240 minutes after the beginning of reaction.

Experiment II: Identification of Decomposition Product of AM Decomposed in Serum Separation of fragment peptides from hAM(1-52) was performed by reverse-phase high-performance liquid chromatography (reverse-phase HPLC) with a Bio-Sil ODS-SIL column (4.0×150 mm, Tosoh Corporation). Elution in the reverse-phase HPLC was performed by using a linear concentration gradient of 6% to 60% aqueous solution of acetonitrile containing 0.1% TFA. Detection for eluates was performed by recording ultraviolet (UV) absorption at a wavelength of 210 nm.

Figure 2:
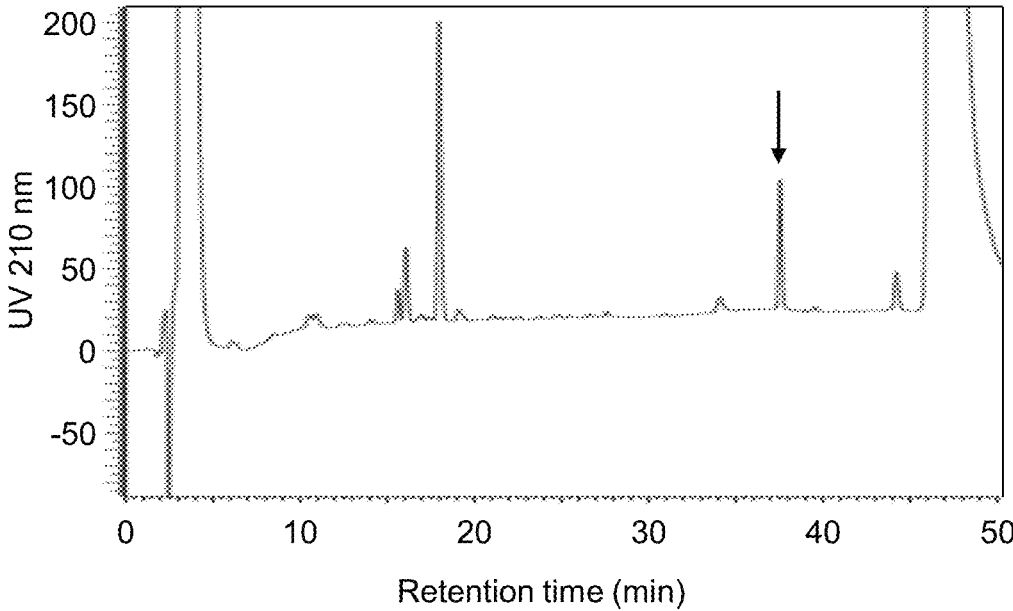
FIG. 2 shows a UV chromatogram at a wavelength of 210 nm by reverse-phase high-performance liquid chromatography (reverse-phase HPLC) for a decomposition product of hAM(1-52) in Experiment II. In the figure, the abscissa represents retention time (min) in reverse-phase HPLC, and the ordinate represents UV absorption intensity at a wavelength of 210 nm.

In serum, 40 μg of synthetic hAM(1-52) was incubated for 4 hours. A decomposition product of hAM(1-52) contained in the resulting reaction mixture was separated by reverse-phase HPLC. FIG. 2 shows the UV chromatogram at a wavelength of 210 nm by reverse-phase HPLC for a decomposition product of hAM(1-52). In the figure, the abscissa represents retention time (min) in reverse-phase HPLC, and the ordinate represents UV absorption intensity at a wavelength of 210 nm.

As shown in FIG. 2, some peaks were detected. Among these peaks, peaks except a peak at a retention time of 37.55 min (indicated by an arrow in the figure) were detected also in a UV chromatogram for a sample of a blank reaction mixture without hAM(1-52) (the UV chromatogram for the blank is not shown). From these results, the peak at a retention time of 37.55 min was determined to correspond to a decomposition product of hAM(1-52). The fraction containing the peak had immunoreactivity to the whole AM, but did not have immunoreactivity to mature AM (data not shown).

Figure 3:
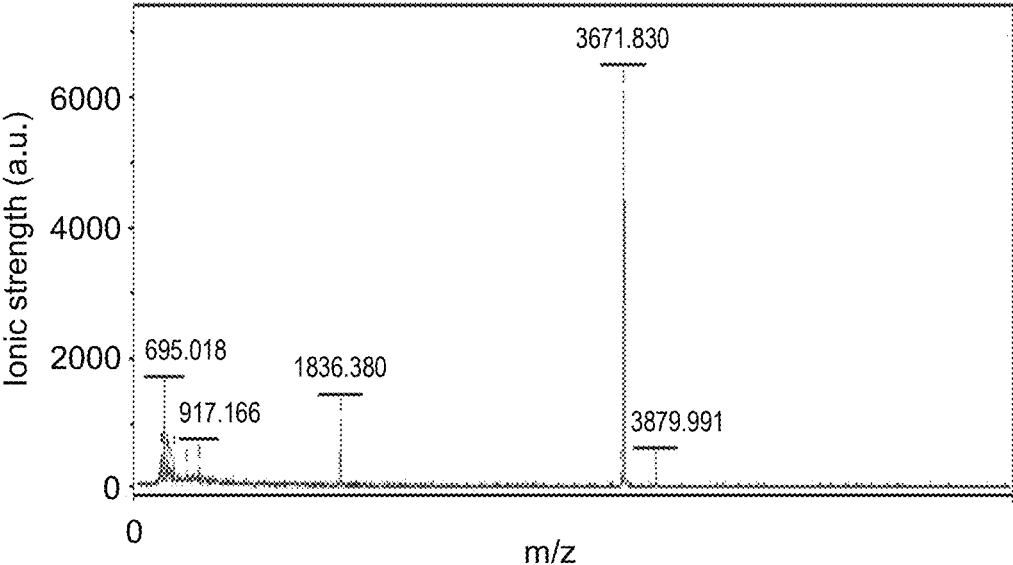
FIG. 3 shows a MALDI-TOFMS spectrum for a purified peptide in Experiment II. In the figure, the abscissa represents mass-to-charge ratios (m/z), and the ordinate represents ionic strength (a.u.).

The fraction containing the peak indicated by an arrow in FIG. 2 was further purified, and the resulting peptide was analyzed with a mass spectrometer (MALDI-TOF, positive ion mode, BRUKER autoflex III). FIG. 3 shows the MALDI-TOFMS spectrum for the purified peptide. In the figure, the abscissa represents mass-to-charge ratios (m/z), and the ordinate represents ionic strength (a.u.).

As shown in FIG. 3, ion peaks at m/z 3671.830 and m/z 1836.380 were detected in the MALDI-TOFMS spectrum for the purified peptide, and these ion peaks respectively corresponded to molecular ions having monovalent and divalent charges ($[M+H]^+$ and $[M+2H]^{2+}$). On the basis of the MALDI-TOFMS spectrum, the molecular weight of the purified peptide was determined to be 3670.8. This molecular weight can correspond to a peptide consisting of amino acid residues at positions 12 to 43 of hAM(1-52) (hAM(12-43)) or a peptide consisting of amino acid residues at positions 13 to 44 of hAM(1-52) (hAM(13-44)). hAM(12-43) and hAM(13-44) have the same amino acid composition and the same precise theoretical molecular weight.

The purified peptide was subjected to amino acid sequence analysis for the N-terminus by using a gas-phase peptide sequencer (apparatus: Applied Biosystems Procise 492HT, method: Pulsed Liquid method). Table 1 shows a result of the amino acid sequence analysis for the N-terminus of the purified peptide. In the table, Cycle shows cycles of the amino acid sequence analysis, corresponding to the position of an amino acid residue from the N-terminus.

TABLE 1

| Cycle | Detected PTH amino acid | Quantitative value (pmol) |
|-------|-------------------------|---------------------------|
| 1 | S | 4.02 |
| 2 | F | 4.96 |
| 3 | G | 6.03 |
| 4 | — | — |
| 5 | R | 2.28 |

From the result of the amino acid sequence analysis shown in Table 1, the amino acid sequence at the amino-terminus was determined to be S-F-G-X-R, and X was expected to be cysteine.

The result determined that the purified peptide was hAM (13-44) (SEQ ID NO: 2). It is estimated that hAM(13-44) was generated through digestion between arginine residue at position 12 and serine residue at position 13 and between arginine residue at position 44 and serine residue at position 45 in hAM(1-52). The results suggest that hAM(1-52) was digested by a trypsin-like protease.

Experiment III: Synthesis of Peptidase-Resistant AM Analogs (1)

AM analog peptides stable in serum were designed as follows. The cyclic structure having a disulfide bond formed by cysteine residues at positions 16 and 21 of hAM(1-52) and the C-terminal amide structure of hAM(1-52) are both essential for AM activity, whereas the peptide structure consisting of amino acid residues at positions 1 to 12 of hAM(1-52) is not essential for AM activity (Eguchi S et al., Endocrinology. December 1994, Volume 135, Issue 6, p. 2454-8). Therefore, a peptide consisting of amino acid residues at positions 13 to 52 of hAM(1-52), being amidated at the C-terminus thereof, and having disulfide bond formed by cysteine residues at positions 4 (corresponding to position 16 of hAM(1-52)) and 9 (corresponding to position 21 of hAM(1-52)) (hAM(13-52)) (SEQ ID NO: 3) was selected as a key molecule. Then, [D-Arg-44]hAM(13-52) (SEQ ID -continued

```
[Lys-44]hAM(13-52)
                                      (SEQ ID NO: 5)
S-F-G-C-R-F-G-T-C-T-V-Q-K-L-A-H-Q-I-Y-Q-F-T-D-K-D-

K-D-N-V-A-P-K-S-K-I-S-P-Q-G-Y-CONH₂
```

```
[Ala-44]hAM(13-52)
                                      (SEQ ID NO: 6)
S-F-G-C-R-F-G-T-C-T-V-Q-K-L-A-H-Q-I-Y-Q-F-T-D-K-D-

K-D-N-V-A-P-A-S-K-I-S-P-Q-G-Y-CONH₂
```

By using the automated peptide synthesizer model ABI 433A (Applied Biosystems) with a 9-fluorenylmethoxycarbonyl (Fmoc) method in accordance with a protocol of the synthesizer, the peptide chains of the three AM analog peptides were elongated with use of Fmoc-Rink Amide resin (0.125 mmol) as a starting raw material, giving protected peptide resins with the AM analog peptides. The protected peptide resins were treated with trifluoroacetic acid for resin removal and deprotection to afford reduced-form crude products of the three AM analog peptides. The reduced-form crude products were oxidized to form a disulfide bond. The reaction products were purified through preparative HPLC to afford the three AM analog peptides having a disulfide bond and a C-terminal amide structure as freeze-dried powders ([D-Arg-44]hAM(13-52): 201 mg, [Lys-44]hAM (13-52): 176 mg, [Ala-44]hAM(13-52): 148 mg). The structure and amino acid sequence of each AM analog peptide were confirmed through preparative HPLC, amino acid analysis, and mass spectrometry. Table 2 shows the results of mass spectrometry by ESI-QMS for the AM analog peptides.

TABLE 2

|  | [D-Arg-44]hAM(13-52) | | [Lys-44]hAM(13-52) | | [Ala-44]hAM(13-52) | |
|---|---|---|---|---|---|---|
|  | Calculated value | Measure-ment | Calculated value | Measure-ment | Calculated value | Measure-ment |
| $[M + 3H]^{3+}$ | 1512.0 | 1511.8 | 1502.7 | 1502.6 | 1483.7 | 1483.6 |
| $[M + 4H]^{4+}$ | 1134.3 | 1134.3 | 1127.3 | 1127.2 | 1113.0 | 1112.9 |
| $[M + 5H]^{5+}$ | 907.6 | 907.7 | 902.0 | 902.0 | 890.6 | 890.5 |
| $[M + 6H]^{6+}$ | 756.5 | 756.5 | 751.8 | 751.8 | 742.3 | 742.3 |
| $[M + 7H]^{7+}$ | 648.6 | 648.5 | 644.6 | 644.7 | 636.4 | 636.5 |
| $[M + 8H]^{8+}$ | 567.6 | 567.7 | 564.1 | 564.2 | 557.0 | N.D. |
| Molecular weight*⁾ | 4533.1 | 4533.1 | 4505.1 | 4505.2 | 4448.0 | 4447.9 |

*⁾In the row of "Molecular weight", each calculated value is a value of average molecular weight based on the molecular formula of the corresponding compound, and each measurement is a deconvoluted value based on a measurement for a polyvalent ion.

NO: 4), [Lys-44]hAM(13-52) (SEQ ID NO: 5), and [Ala-44]hAM(13-52) (SEQ ID NO: 6) were designed, each being an AM analog peptide with arginine residue at position 32 of hAM(13-52) (corresponding to position 44 of hAM(1-52)) substituted with D-arginine (D-Arg), L-lysine (Lys), or L-alanine (Ala).

```
Amino acid sequences of AM analog peptides
hAM(13-52)
                                      (SEQ ID NO: 3)
S-F-G-C-R-F-G-T-C-T-V-Q-K-L-A-H-Q-I-Y-Q-F-T-D-K-D-

K-D-N-V-A-P-R-S-K-I-S-P-Q-G-Y-CONH₂
```

```
[D-Arg-44]hAM(13-52)
              (SEQ ID NO: 4, "*R" denotes D-arginine)
S-F-G-C-R-F-G-T-C-T-V-Q-K-L-A-H-Q-I-Y-Q-F-T-D-K-D-

K-D-N-V-A-P-*R-S-K-I-S-P-Q-G-Y-CONH₂
```

Experiment IV: Stabilities of AM Analogs in Serum (1)

Figure 4:
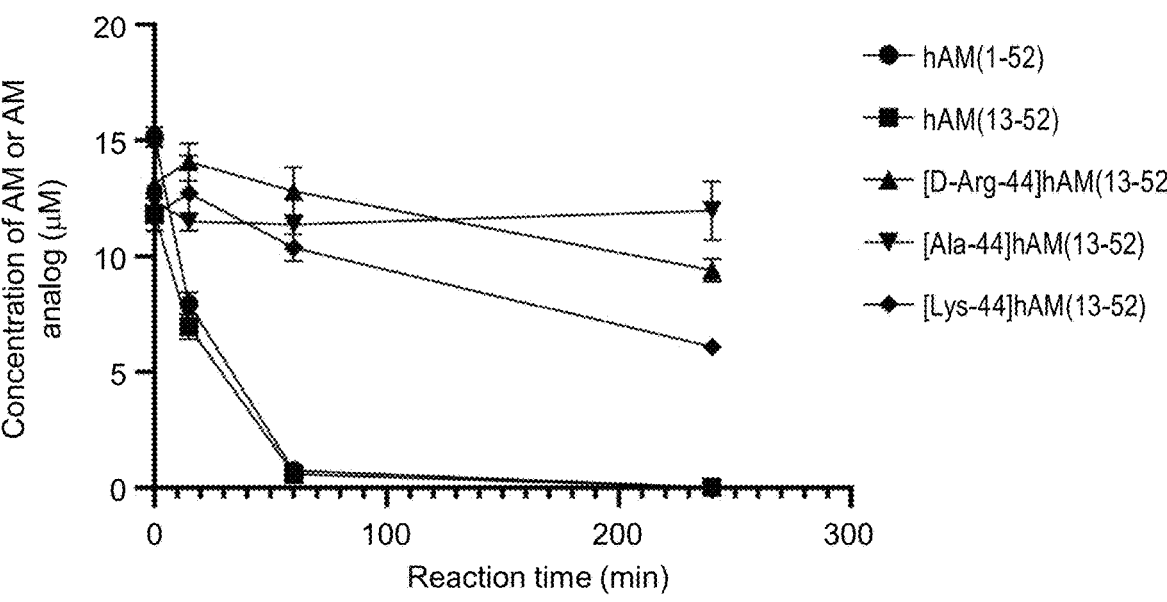
FIG. 4 shows time course of concentration of AM or an AM analog contained in samples of a reaction mixture with serum in Experiment IV. In the figure, the abscissa represents reaction time (min), and the ordinate represents concentration of AM or an AM analog (UM).

The stabilities of hAM(13-52), [D-Arg-44]hAM(13-52), [Lys-44]hAM(13-52), and [Ala-44]hAM(13-52) in serum were evaluated with the same procedure as in Experiment I. Mature AM (hAM(1-52)) was used as a control. Because the AM analogs each exhibit immune activity similar to that of hAM(1-52) in specific fluoroimmunoassay in Experiment I, they allow quantitative analysis using the specific fluoroimmunoassay like hAM(1-52). FIG. 4 shows time course of concentration of AM or an AM analog contained in samples of a reaction mixture with serum. In the figure, the abscissa represents reaction time (min), and the ordinate represents concentration of AM or an AM analog (μM).

As shown in FIG. 4, for each of the reaction mixtures of hAM(1-52) and hAM(13-52), the amount of AM or an AM analog rapidly decreased with the lapse of reaction time in the reaction mixture with serum, a concentration of 1 μM or less was reached 60 minutes after the beginning of reaction, and a concentration below the detection limit was reached 240 minutes after the beginning of reaction. For the reaction mixtures of [D-Arg-44]hAM(13-52), [Lys-44]hAM(13-52), and [Ala-44]hAM(13-52), by contrast, each of these AM analogs underwent almost no decrease or only slight decrease in amount even after the lapse of reaction time in the reaction mixture with serum, and a certain amount thereof remained even 240 minutes after the beginning of reaction.

Figure 5:
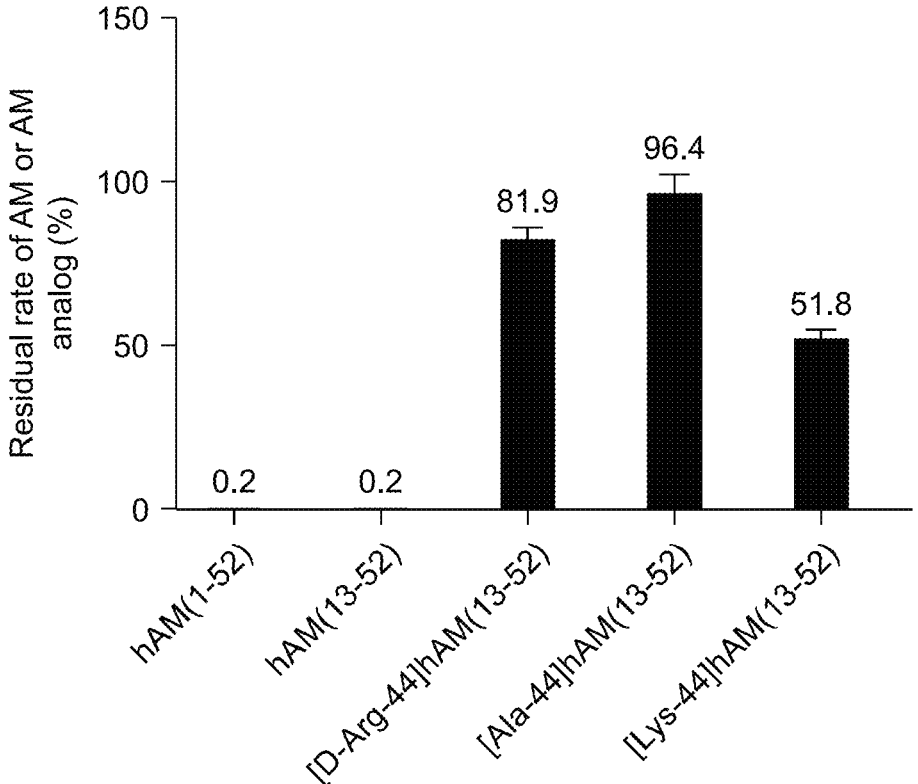
FIG. 5 shows residual rates of AM or an AM analog in a reaction mixture 240 minutes after the beginning of reaction of the AM or AM analog in Experiment IV. In the figure, the abscissa represents the type of AM or an AM analog, and the ordinate represents residual rates of AM or an AM analog (%).

In the results, the percentage of the concentration of AM or an AM analog 240 minutes after the beginning of reaction to the concentration of the AM or AM analog at the beginning of reaction (i.e., 0 minutes after the beginning of reaction) was calculated as the residual rate (%). FIG. 5 shows residual rates of AM or an AM analog in a reaction mixture 240 minutes after the beginning of reaction of the AM or AM analog. In the figure, the abscissa represents the type of AM or an AM analog, and the ordinate represents residual rates of AM or an AM analog (%).

As shown in FIG. 5, in each of the reaction mixtures of hAM(1-52) and hAM(13-52), the residual rate of the AM or AM analog was 0.2%. By contrast, the residual rates of an AM analog in the reaction mixtures of [D-Arg-44]hAM(13-52), [Ala-44]hAM(13-52), and [Lys-44]hAM(13-52) were 81.9, 96.4, and 51.8%, respectively. The results of the present experiment revealed that the novel AM analogs [D-Arg-44]hAM(13-52), [Ala-44]hAM(13-52), and [Lys-44]hAM(13-52) each have significantly higher stability in serum than hAM(1-52), which is natural AM, and hAM(13-52), which is an N-terminus-deleted peptide of hAM(1-52).

Experiment V: Intracellular cAMP Concentration-Increasing Effects of AM Analogs (1)

Figure 6:
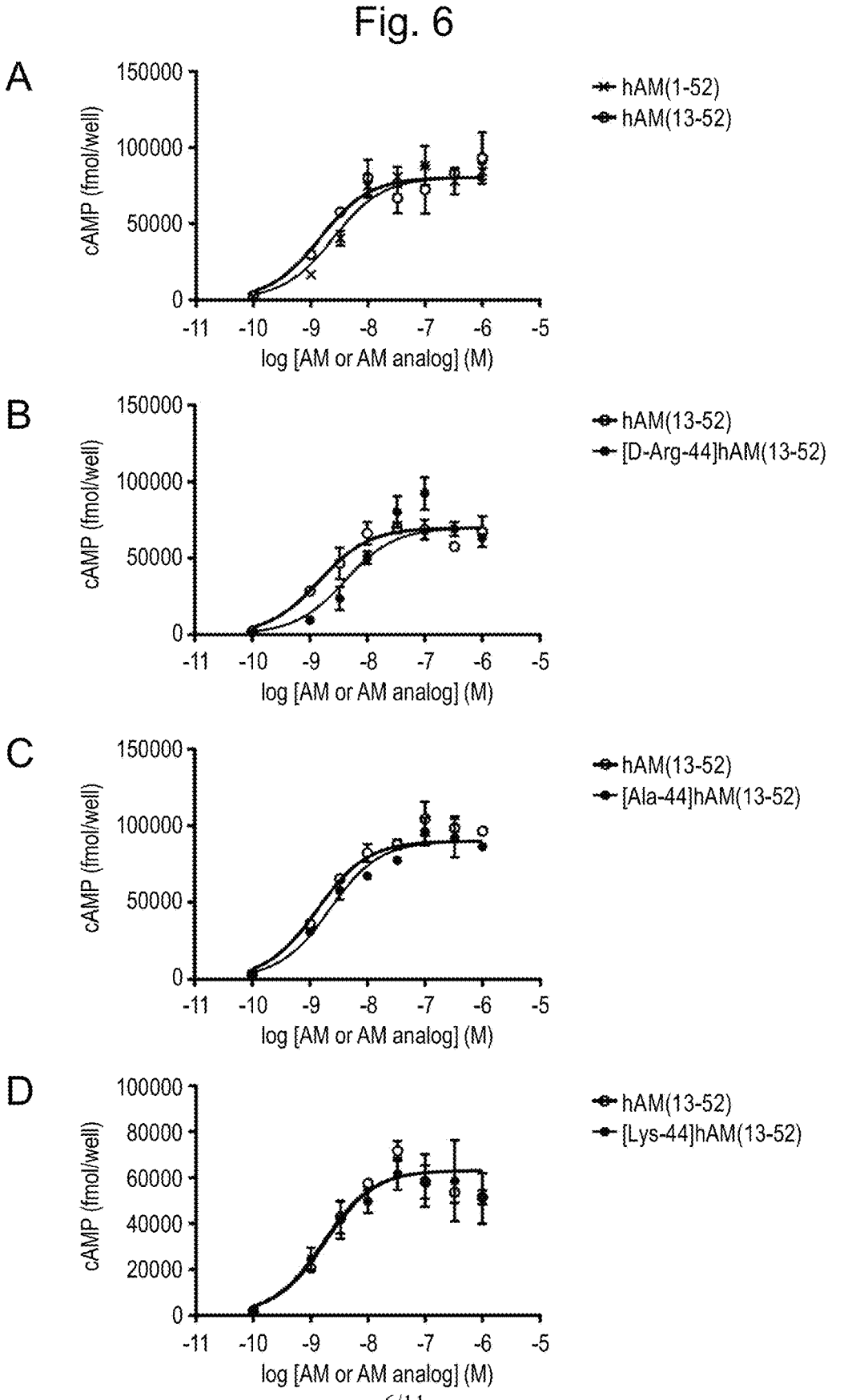
FIG. 6 shows dose-response curves of amounts of intracellular cAMP produced in HEK293 cells to concentration of AM or an AM analog added in Experiment V. In the figure, A shows results of an experiment with addition of hAM(1-52) (cross) or hAM(13-52) (open circle), B shows results of an experiment with addition of hAM(13-52) (open circle) or [D-Arg-44]hAM(13-52) (solid circle), C shows results of an experiment with addition of hAM(13-52) (open circle) or [Ala-44]hAM(13-52) (solid circle), and D shows results of an experiment with addition of hAM(13-52) (open circle) or [Lys-44]hAM(13-52) (solid circle). In the figure, the abscissa represents logarithms of concentration of AM or an AM analog added (M), and the ordinate represents amounts of intracellular cAMP produced in HEK293 cells stably expressing an AMI receptor (fmol/well).

The physiological effect of AM is known to be exerted via increase in the concentration of intracellular cAMP (see Kitamura K et al., Biochem Biophys Res Commun, 30 Apr. 1993, Volume 192, Issue 2, pp. 553-560). Accordingly, each AM analog was added to a cultured cell line (HEK293 cell line) caused to stably express an AM type 1 receptor (AMI receptor), and the amount of intracellular cAMP produced was measured. HEK293 cells were cultured in Dulbecco's modified Eagle's medium (with 10% fetal bovine serum, 100 U/ml penicillin G, 100 mg/ml streptomycin, 0.25 mg/ml amphotericin B, 100 mg/ml hygromycin B, and 250 mg/ml Geneticin) in a fibronectin-coated 24-well plate (Thermo Fisher Scientific) (under 37° C., humidified, 5% $CO_2$ conditions). After culturing for 3 days, 90%-confluent cells with accumulation of intracellular cAMP stimulated were subjected to experiment. The medium was exchanged with Hanks's balanced salt solution containing 20 mM 4-(2-hydroxyethyl)-1-piperazineethanesulfonic acid and 0.1% bovine serum albumin, AM or an AM analog was added to the cells in the presence of 0.5 mM isobutylmethylxanthine (IBMX), and the cells were incubated at 37° C. for 15 minutes. The reaction was terminated by addition of cell lysis buffer. Then, the amount of intracellular cAMP produced in the HEK293 cells of each well was measured using an ELISA kit for cAMP measurement (GE Healthcare Japan Corp., #RPN2251). FIG. 6 shows dose-response curves of amounts of intracellular cAMP produced in HEK293 cells to concentration of AM or an AM analog added. In the figure, A shows results of an experiment with addition of hAM(1-52) (cross) or hAM(13-52) (open circle), B shows results of an experiment with addition of hAM(13-52) (open circle) or [D-Arg-44]hAM(13-52) (solid circle), C shows results of an experiment with addition of hAM(13-52) (open circle) or [Ala-44]hAM(13-52) (solid circle), and D shows results of an experiment with addition of hAM(13-52) (open circle) or [Lys-44]hAM(13-52) (solid circle). In the figure, the abscissa represents logarithms of concentration of AM or an AM analog added (M), and the ordinate represents amounts of intracellular cAMP produced in HEK293 cells stably expressing an AMI receptor (fmol/well).

As shown in FIG. 6, all the AM analog peptides were revealed to exhibit intracellular cAMP concentration-increasing activity approximately equivalent to that of hAM (1-52) or hAM(13-52).

Experiment VI: Comparison of Pharmacokinetics Between AM and AM Analogs (1)

Figure 7:
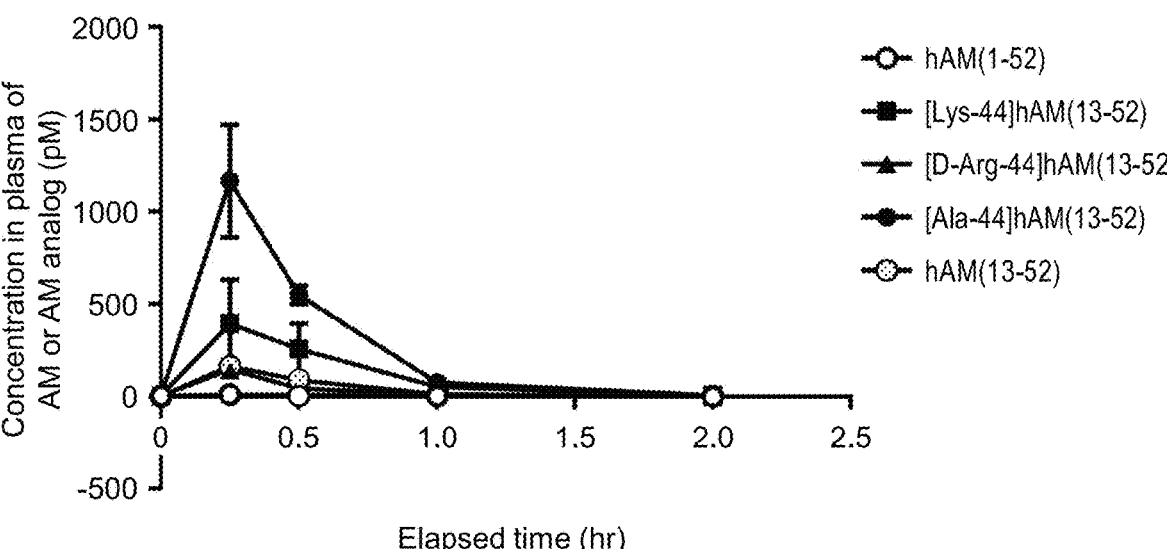
FIG. 7 shows time course of amounts of AM or an AM analog in rat plasma after subcutaneous administration in Experiment VI. In the figure, the abscissa represents elapsed time after subcutaneous administration (hr), and the ordinate represents concentration in plasma of AM or an AM analog (pM).

Eight-week-old male Wistar rats were purchased from Charles River Laboratories Japan, Inc. The rats were grown with normal feeds in the absence of specific pathogens under cycles of a 12-hour light period and a 12-hour dark period. Experiments were conducted under approval by the Animal Experiment Committee of University of Miyazaki (2014-507-4) in accordance with animal protection laws. To determine plasma AM concentrations, 50 nmol/kg of AM or an AM analog was subcutaneously administered. A peripheral blood sample was collected from the tail vein into a test tube (containing 21 μg of aprotinin and 0.3 mg of EDTA-2Na) at predetermined times (0, 15, 30, 60, and 120 minutes after administration). The test tube was centrifuged at 1,700×g to afford plasma. The amount of AM or an AM analog in rat plasma was measured through specific fluoroimmunoassay with the same procedure as in Experiment I. FIG. 7 shows time course of amounts of AM or an AM analog in rat plasma after subcutaneous administration. In the figure, the abscissa represents elapsed time after subcutaneous administration (hr), and the ordinate represents concentration in plasma of AM or an AM analog (pM). Table 3 shows maximum concentration in blood (Cmax), concentration in blood-time area under the curve (AUC), and blood half-life for AM or AM analogs in rat plasma after subcutaneous administration.

TABLE 3

| | hAM(1-52) | hAM(13-52) | [D-Arg-44] hAM(13-52) | [Lys-44] hAM(13-52) | [Ala-44] hAM(13-52) |
|---|---|---|---|---|---|
| Maximum concentration in blood (Cmax, pM) | 10.79 | 164.9 | 110.8 | 395.7 | 1165 |
| Concentration in blood-time area under the curve (AUC, pM · hr) | 40.97 | 83.23 | 59.09 | 226.5 | 577.6 |

TABLE 3-continued

|  | hAM(1-52) | hAM(13-52) | [D-Arg-44] hAM(13-52) | [Lys-44] hAM(13-52) | [Ala-44] hAM(13-52) |
|---|---|---|---|---|---|
| Blood half-life (hr) | 1.228 | 1.406 | 1.271 | 1.471 | 1.373 |

As shown in FIG. 7, hAM(1-52) and hAM(13-52) were hardly detected in rat plasma. By contrast, the AM analogs [D-Arg-44]hAM(13-52), [Ala-44]hAM(13-52), and [Lys-44]hAM(13-52) were detected in rat plasma 15 minutes after administration, and each exhibited high Cmax and AUC. In particular, [Ala-44]hAM(13-52) exhibited Cmax 100 times or more higher than that of hAM(1-52) (Table 3). The results of the present experiment revealed that the novel AM analogs [D-Arg-44]hAM(13-52), [Ala-44]hAM(13-52), and [Lys-44]hAM(13-52) exhibit significantly superior pharmacokinetics with respect to biological stability to hAM(1-52), which is natural AM, and hAM(13-52), which is an N-terminus-deleted peptide of hAM(1-52), in single administration.

Experiment VII: Synthesis of AM Analogs (2)

AM analog peptides stable in serum were designed as follows. Designed were [Gly-44]hAM(13-52) (SEQ ID NO: 7), [Asp-44]hAM(13-52) (SEQ ID NO: 9), and [Phe-44] hAM(13-52) (SEQ ID NO: 10), each being an AM analog peptide obtained by substituting arginine residue at position 32 of hAM(13-52) (SEQ ID NO: 3) (corresponding to position 44 of hAM(1-52)) with glycine (Gly), L-aspartic acid (Asp), or L-phenylalanine (Phe), [Pro-45]hAM(13-52) (SEQ ID NO: 11), being an AM analog peptide obtained by substituting serine residue at position 33 of hAM(13-52) (SEQ ID NO: 3) (corresponding to position 45 of hAM(1-52)) with L-proline (Pro), and [des-Arg-44]hAM(13-52) (SEQ ID NO: 8), being an AM analog peptide obtained by deleting arginine residue at position 32 of hAM(13-52) (SEQ ID NO: 3) (corresponding to position 44 of hAM(1-52)). hAM(1-52) was purchased from PEPTIDE INSTITUTE, INC. (Osaka, Japan). Synthesis of hAM(13-52), [Ala-44]hAM(13-52), [D-Arg-44]hAM(13-52), [Lys-44] hAM(13-52), [Gly-44]hAM(13-52), [des-Arg-44]hAM(13-52), [Asp-44]hAM(13-52), [Phe-44]hAM(13-52), and [Pro-45]hAM(13-52) was outsourced to PEPTIDE INSTITUTE, INC.

```
Amino acid sequences of AM analog peptides
hAM(13-52)
                                   (SEQ ID NO: 3)
S-F-G-C-R-F-G-T-C-T-V-Q-K-L-A-H-Q-I-Y-Q-F-T-D-K-D-

K-D-N-V-A-P-R-S-K-I-S-P-Q-G-Y-CONH₂

[Gly-44]hAM(13-52)
                                   (SEQ ID NO: 7)
S-F-G-C-R-F-G-T-C-T-V-Q-K-L-A-H-Q-I-Y-Q-F-T-D-K-D-

K-D-N-V-A-P-G-S-K-I-S-P-Q-G-Y-CONH₂

[des-Arg-44]hAM(13-52)
                                   (SEQ ID NO: 8)
S-F-G-C-R-F-G-T-C-T-V-Q-K-L-A-H-Q-I-Y-Q-F-T-D-K-D-

K-D-N-V-A-P-S-K-I-S-P-Q-G-Y-CONH₂
```

```
                              -continued
[Asp-44]hAM(13-52)
                                   (SEQ ID NO: 9)
S-F-G-C-R-F-G-T-C-T-V-Q-K-L-A-H-Q-I-Y-Q-F-T-D-K-D-

K-D-N-V-A-P-D-S-K-I-S-P-Q-G-Y-CONH₂

[Phe-44]hAM(13-52)
                                   (SEQ ID NO: 10)
S-F-G-C-R-F-G-T-C-T-V-Q-K-L-A-H-Q-I-Y-Q-F-T-D-K-D-

K-D-N-V-A-P-F-S-K-I-S-P-Q-G-Y-CONH₂

[Pro-45]hAM(13-52)
                                   (SEQ ID NO: 11)
S-F-G-C-R-F-G-T-C-T-V-Q-K-L-A-H-Q-I-Y-Q-F-T-D-K-D-

K-D-N-V-A-P-R-P-K-I-S-P-Q-G-Y-CONH₂
```

Experiment VIII: Stabilities of AM Analogs in Serum (2)

Figure 8:
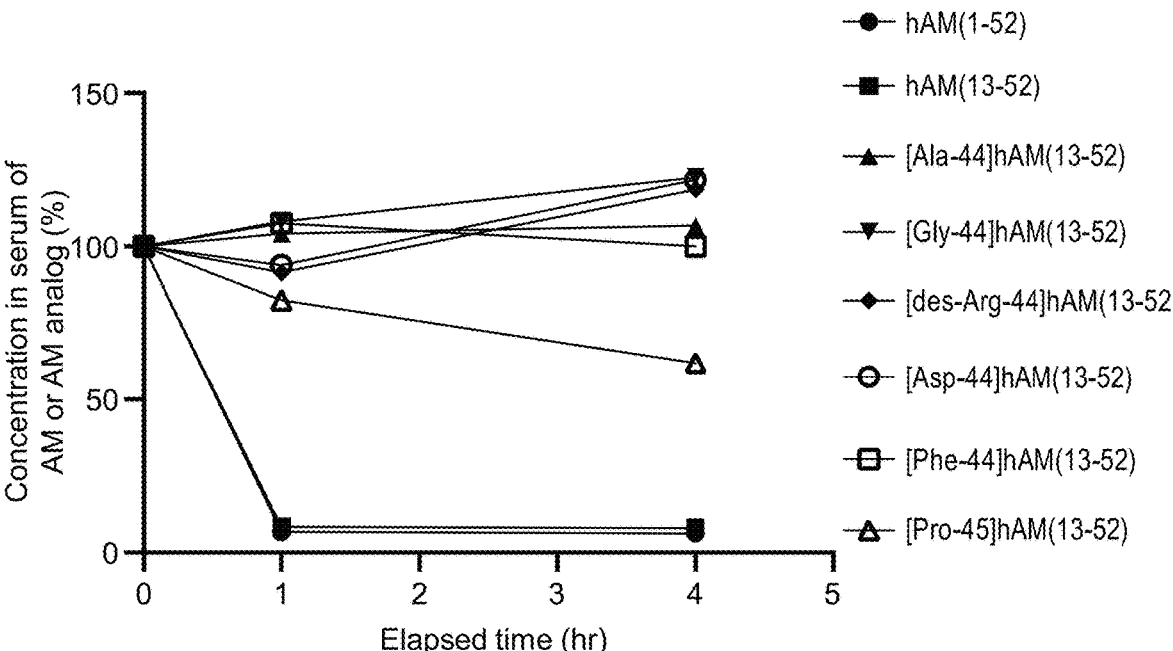
FIG. 8 shows time course of concentration of AM or an AM analog contained in samples of a reaction mixture with serum in Experiment VIII. In the figure, the abscissa represents reaction time (hr), and the ordinate represents concentration in serum of AM or an AM analog (%) represented as relative values to concentration of AM or an AM analog at the beginning of reaction (i.e., 0 hours after the beginning of reaction).

The stabilities of the AM analog peptides in serum were evaluated with the same procedure as in Experiment I except the following procedure. Mature AM (hAM(1-52)) was used as a control. A reaction mixture containing 4 μL of phosphate buffer, 20 μL of human serum (Sigma-Aldrich Co. LLC, USA), and 14 μL of water was prepared. To the reaction mixture, 2 μL of AM or an AM analog peptide ($2\times10^{-6}$ M, final concentration: $10^{-7}$ M) was added, and reaction was initiated at 37° C. The reaction was terminated by addition of 160 μL of ELISA buffer to the reaction mixture 0, 1, or 4 hours after the beginning of reaction. The concentration of AM or an AM analog peptide contained in samples of a reaction mixture with serum was measured by using specific fluoroimmunoassay with the same procedure as in Experiment I. FIG. 8 shows time course of concentration of AM or an AM analog contained in samples of a reaction mixture with serum. In the figure, the abscissa represents reaction time (hr), and the ordinate represents concentration in serum of AM or an AM analog (%) represented as relative values to concentration of AM or an AM analog at the beginning of reaction (i.e., 0 hours after the beginning of reaction).

As shown in FIG. 8, for each of the reaction mixtures of hAM(1-52) and hAM(13-52), AM or an AM analog substantially disappeared from the reaction mixture with serum 1 hour after the beginning of reaction. By contrast, [Gly-44]hAM(13-52), [des-Arg-44]hAM(13-52), [Asp-44]hAM(13-52), and [Phe-44]hAM(13-52) were stable even 4 hours after the beginning of reaction. The amount of [Pro-45]hAM(13-52) decreased to a concentration of about 60% 4 hours after the beginning of reaction.

Experiment IX: Intracellular cAMP Concentration-Increasing Effects of AM Analogs (2)

Figure 9:
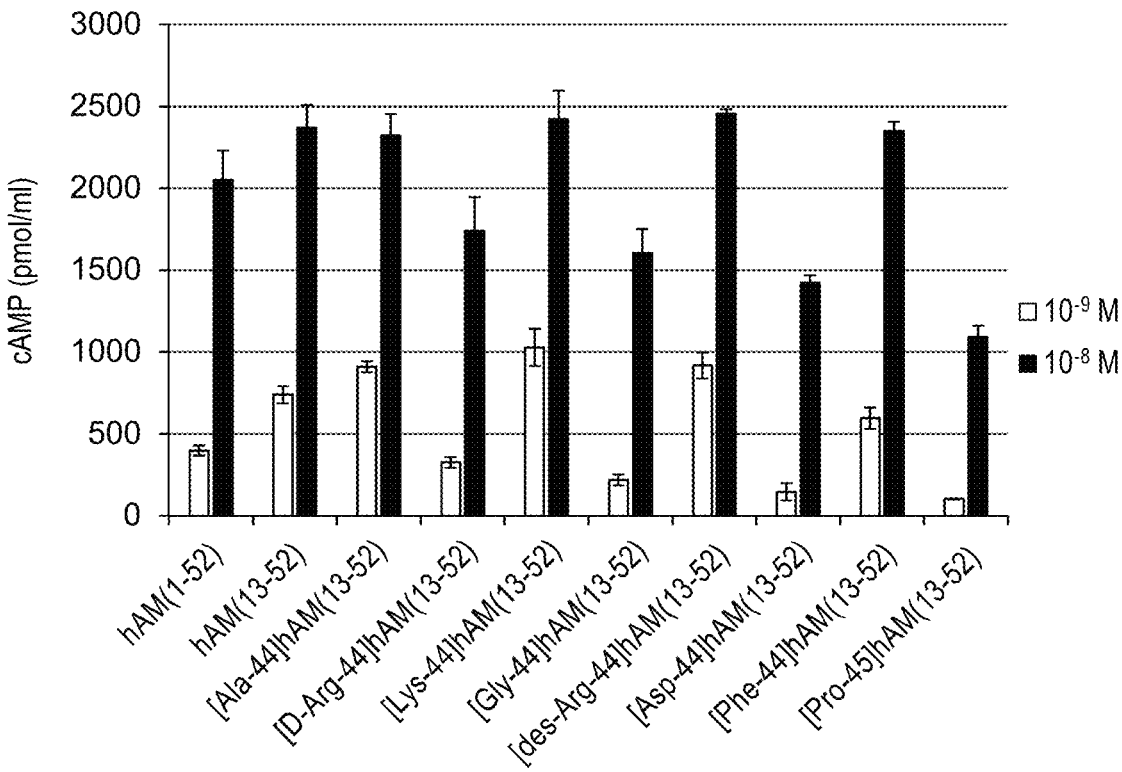
FIG. 9 shows amounts of intracellular cAMP produced in HEK293 cells for addition of AM or an AM analog at $10^{-9}$ M or $10^{-8}$ M in Experiment IX. In the figure, the ordinate represents amounts of intracellular cAMP produced in HEK293 cells stably expressing an AMI receptor (fmol/ml).

The intracellular cAMP concentration-increasing effects of the AM analogs were evaluated with the same procedure as in Experiment V. FIG. 9 shows amounts of intracellular cAMP produced in HEK293 cells for addition of AM or an AM analog at $10^{-9}$ M or $10^{-8}$ M. In the figure, the ordinate represents amounts of intracellular cAMP produced in HEK293 cells stably expressing an AMI receptor (fmol/ml).

As shown in FIG. 9, the AM analog peptides [Gly-44] hAM(13-52), [des-Arg-44]hAM(13-52), and [Phe-44]hAM (13-52) were revealed to exhibit intracellular cAMP concentration-increasing activity approximately equivalent to that of hAM(1-52) or hAM(13-52).

Figure 10:
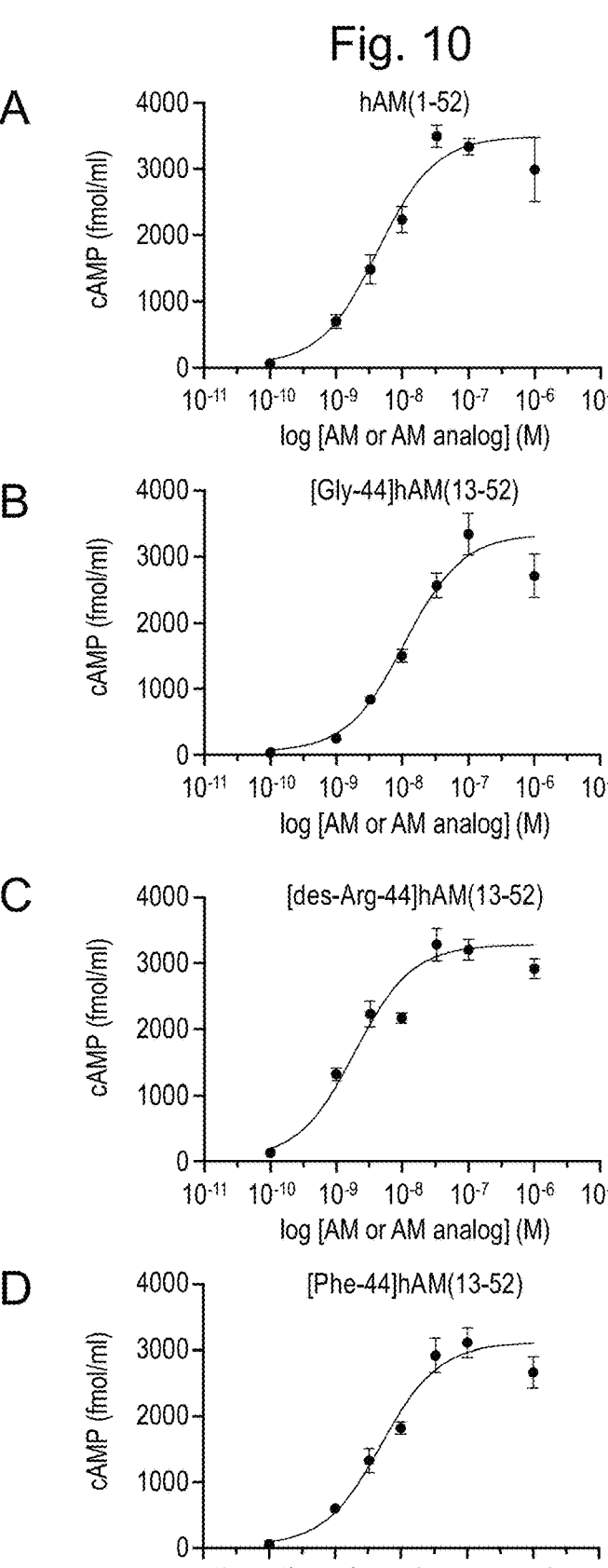
FIG. 10 shows dose-response curves of amounts of intracellular cAMP produced in HEK293 cells to concentration of AM or an AM analog added in Experiment IX. In the figure, A shows results of an experiment with addition of hAM(1-52), B shows results of an experiment with addition of [Gly-44]hAM(13-52), C shows results of an experiment with addition of [des-Arg-44]hAM(13-52), and D shows results of an experiment with addition of [Phe-44]hAM(13-52). In the figure, the abscissa represents logarithms of concentration of AM or an AM analog added (M), and the ordinate represents amounts of intracellular cAMP produced in HEK293 cells stably expressing an AMI receptor (fmol/ml).

For the AM analog peptides [Gly-44]hAM(13-52), [des-Arg-44]hAM(13-52), and [Phe-44]hAM(13-52), which exhibited intracellular cAMP concentration-increasing activity approximately equivalent to that of hAM(1-52) or hAM(13-52) in FIG. 9, dose response of amounts of intracellular cAMP produced was evaluated. FIG. 10 shows dose-response curves of amounts of intracellular cAMP produced in HEK293 cells to concentration of AM or an AM analog added. In the figure, A shows results of an experiment with addition of hAM(1-52), B shows results of an experiment with addition of [Gly-44]hAM(13-52), C shows results of an experiment with addition of [des-Arg-44]hAM(13-52), and D shows results of an experiment with addition of [Phe-44]hAM(13-52). In the figure, the abscissa represents logarithms of concentration of AM or an AM analog added (M), and the ordinate represents amounts of intracellular cAMP produced in HEK293 cells stably expressing an AMI receptor (fmol/ml).

As shown in FIG. 10, all the AM analog peptides caused increase in intracellular cAMP concentration in a manner depending on concentration of an AM analog peptide added. In addition, all the AM analog peptides were revealed to exhibit largest activity for increase in intracellular cAMP concentration approximately equivalent to that of hAM(1-52) or hAM(13-52). For intracellular cAMP concentration-increasing activity, logarithmic values of 50%-effective concentration (pEC50) were calculated to be 8.37 for hAM(1-52), and 7.96 for [Gly-44]hAM(13-52), 8.71 for [des-Arg-44]hAM(13-52), and 8.29 for [Phe-44]hAM(13-52).

Experiment X: Comparison of Pharmacokinetics Between AM and AM Analogs (2)

Figure 11:
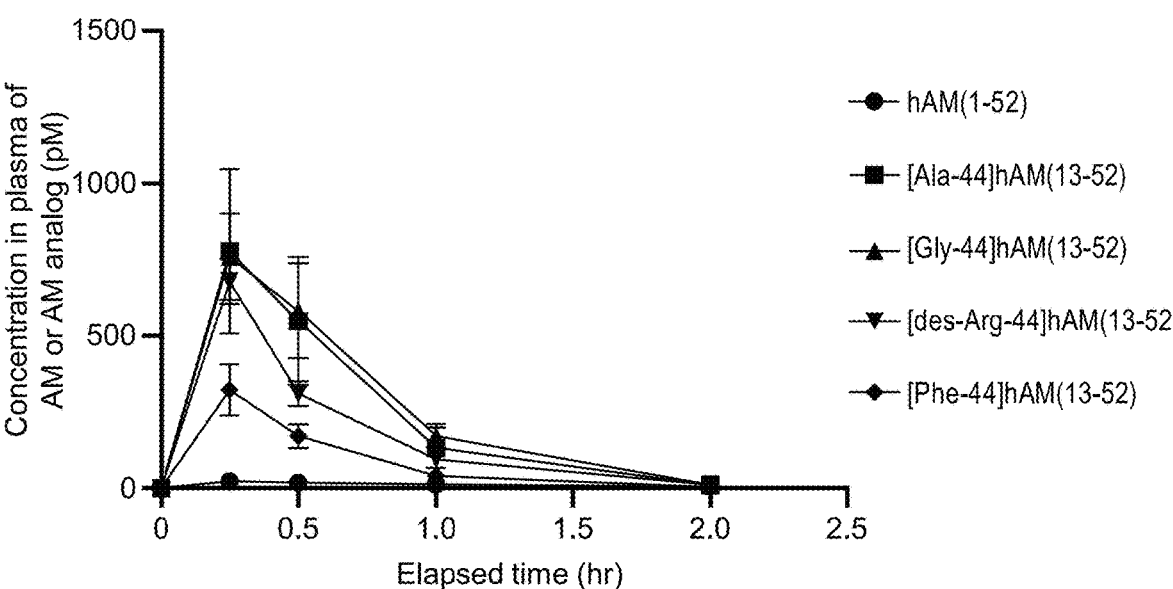
FIG. 11 shows time course of amounts of AM or an AM analog in rat plasma after subcutaneous administration in Experiment X. In the figure, the abscissa represents elapsed time after subcutaneous administration (hr), and the ordinate represents concentration in plasma of AM or an AM analog (pM).

The pharmacokinetics of AM and the AM analogs (hAM (1-52), [Ala-44]hAM(13-52), [Gly-44]hAM(13-52), [des-Arg-44]hAM(13-52), and [Phe-44]hAM(13-52)) were evaluated with the same procedure as in Experiment VI except the following procedure. Seven-week-old male Wistar rats were prepared, and grown with normal feeds. To determine plasma AM concentrations, 50 nmol/kg of AM or an AM analog was subcutaneously administered. A peripheral blood sample was collected from the tail vein into a Kantan tube® (containing heparin Na, Eiken Chemical Co., Ltd., Tochigi, Japan) at predetermined times (0, 15, 30, 60, and 120 minutes after administration). The tube was centrifuged at 2,000×g. Plasma was collected from the tube, and transferred into a test tube (containing 21 µg of aprotinin and 0.3 mg of EDTA-2Na) and stored. The amount of AM or an AM analog in rat plasma was measured through specific fluoroimmunoassay with the same procedure as in Experiment I. FIG. 11 shows time course of amounts of AM or an AM analog in rat plasma after subcutaneous administration. In the figure, the abscissa represents elapsed time after subcutaneous administration (hr), and the ordinate represents concentration in plasma of AM or an AM analog (pM). In addition, maximum concentrations in blood (Cmax) of AM or the AM analogs in rat plasma after subcutaneous administration were calculated.

As shown in FIG. 11, hAM(1-52) was hardly detected in rat plasma. By contrast, the AM analogs [Ala-44]hAM(13-52), [Gly-44]hAM(13-52), [des-Arg-44]hAM(13-52), and [Phe-44]hAM(13-52) were detected in rat plasma 15 minutes after administration, and each exhibited high Cmax. Calculation of Cmax gave 23.1 pM for hAM(1-52), and 777.0 pM for [Ala-44]hAM(13-52), 760.4 pM for [Gly-44] hAM(13-52), 679.0 pM for [des-Arg-44]hAM(13-52), and 323.3 pM for [Phe-44]hAM(13-52). The results of the present experiment revealed that the novel AM analogs [Ala-44]hAM(13-52), [Gly-44]hAM(13-52), [des-Arg-44] hAM(13-52), and [Phe-44]hAM(13-52) exhibit significantly superior pharmacokinetics with respect to biological stability to hAM(1-52), which is natural AM, in single administration.

Experiment XI: Effect of AM Analog on Influenzavirus-Infected Mice

Drug efficacy test for influenzavirus-infected mice was conducted with use of the AM analog peptide [Ala-44]hAM (13-52) to evaluate the effect of the AM analog on organ dysfunctions in influenzavirus-infected mice.

[XI-1: Test Drug]

A freeze-dried powder of [Ala-44]hAM(13-52) was used as an active ingredient. Aqueous solution of 3.75 w/v % mannitol-0.5 w/v % glycine was used as a medium. To a vial containing the active ingredient, 0.95 mL of the medium was added to dissolve the active ingredient; thus, specimen solution was prepared. The specimen solution was aliquoted into 40-µl portions, which were cryopreserved at −20 to −30° C. The specimen solution was thawed in use, and diluted with the medium to prepare 20 nmol/ml or 2 nmol/ml specimen solution. Each specimen solution was prepared at time of use.

XI-2: Test Virus Strain (a) Virus Strain and Host Cells Therefor

The influenzavirus PR8 (A/PR/8/34 (H1N1)), a stored strain possessed by Department of Microbiology and Immunology, School of Medicine, Aichi Medical University, was used as a virus strain for use in the test.

[XI-3: Drug Efficacy Test on Influenzavirus-Infected Mice]

Forty-five 5-week-old female SPF mice (BALB/c type (BALB/c Cr Slc)) were purchased (Japan SLC, Inc.). After a preliminary growing period for 5 days, the mice were grouped into a control group without administration of the AM analog, a group with administration of the AM analog at low dose (10 nmol/kg), and a group with administration of the AM analog at high dose (100 nmol/kg) (eight mice in each group). For each mouse in each group, the specimen solution was inoculated into the tail vein by using a 27G Winged Needle for vein (Terumo Corporation) and 1.0-ml Polypropylene Disposable Syringe (Terumo Corporation). The liquid volume of the specimen solution to be administered was calculated to set to 5 ml/kg on the basis of values of body weight on the day of administration. The time of administration of the specimen solution was set between 9:25 and 11:27. Exceptionally, on the day of virus inoculation, administration of the specimen solution was performed before the inoculation. The period of administration of the specimen solution was set between the day before virus inoculation and day 4 after inoculation. On the day of virus inoculation, for the mice of the control group without administration of the AM analog and the mice of the groups with administration of the AM analog, 0.05 ml of the solution of the virus to be inoculated per individual ($1\times10^5$ PFU/mouse) was dropped into the nasal cavity by using a micropipette immediately after administration of specimen solution. The solution of the virus to be inoculated was stirred for every inoculation. Growing was continued until day 5 after inoculation, as the day after the inoculation was defined as day 1 after inoculation. The following items were evaluated over the growing period.

(a) General Condition

General condition was observed once per day after the day of grouping on the basis of general condition scores shown in Table 4 in the following.

TABLE 4

| Score | Site of occurrence | | | |
| | (1) Eye | (2) Hair coat | (3) Behavior | (4) Others |
| --- | --- | --- | --- | --- |
| 3 | Blepharosynechia (condition such that eyelids do not open) | Very poor coat | Reduced locomotion (condition such that no movement is present even on contact) | Respiratory failure, leanness, prone position, hypothermal condition |
| 2 | Loss of eyelid reflex (condition such that eyelids open on contact but exhibit no blink reflex) | Dull hair, standing hair | Reduced locomotion (condition such that movement appears on contact) | Irregular respiration (clear), leanness |
| 1 | Closed eyelids (eyelids open on contact) | Slightly standing hair | Showing interests in surroundings, responding to stimuli | Irregular respiration (tachypnea or bradypnea) |
| 0 | Normal (shiny eyes) | Normal (a good coat) | Normal | Normal (without disorder of respiration and others) |

(b) Gross Lesion Examination of Lung

On day 5 after virus inoculation, anesthesia was performed with isoflurane, and approximately 0.3 mL of blood was then collected from the caudal vena cava by using a syringe (Terumo Corporation) treated with EDTA-2Na. The blood obtained was centrifuged (approximately 4° C., 3000 rpm, 2150×g, for 10 minutes) to collect plasma, which was cryopreserved (-80° C.). The animals subjected to blood collection were euthanized by bleeding from the abdominal aorta. Gross examination of lungs was performed separately for the left lung and the right lung on the basis of an evaluation method shown in Table 5 below. Thereafter, the left lung, the right lung, the kidneys, and the heart were excised, and weighted with an electronic balance. The heart excised was horizontally sectioned into three parts. The central part of the heart was soaked in 10% neutral buffered formalin and stored. The residual upper and lower parts of the heart were put in separate tubes, and cryopreserved (-80° C.). Each of the kidneys excised was horizontally sectioned into three parts. The right kidney parts were cryopreserved (-80° C.). The left kidney parts were soaked in 10% neutral buffered formalin and stored. The liver excised was vertically sectioned into two parts, each of which was further horizontally sectioned into three parts. One part of the liver was cryopreserved (-80° C.). The rest parts of the liver were soaked in 10% neutral buffered formalin and stored. For the lungs excised, a part of the left lung (approximately 10 to 20 mg) was cryopreserved (-80° C.). The residual part of the left lung was soaked in 10% neutral buffered formalin and stored. The right lung was used for virological examination.

TABLE 5

| Score | Finding in gross observation for lung lesion |
| --- | --- |
| 4 | Consolidation was found totally |
| 3 | Consolidation was found in ½ to ⅔ |
| 2 | Consolidation was found in ⅓ to ½ |
| 1 | Consolidation was found in from very few to ⅓ |
| 0 | No consolidation was found |

(c) Virus Counting

The right lung excised was finely fragmented, to which 2 ml of Hanks's balanced salt solution (HBSS) was then added, and the resultant was homogenized by using a stirrer (Homogenizer T10 Basic, IKA Japan, K.K.). The resulting homogenate solution was cryopreserved as lung tissue solution. The lung tissue solution was thawed, and diluted solutions thereof were appropriately prepared with MEM. To a 12-well plate on which MDCK cells had been seeded, the stock solution and diluted lung tissue solutions were added at a volume of 0.1 ml per well to allow the cells to adsorb the virus for 1 hour. Onto the cells, culture medium for plaque counting in a volume of 1.5 ml was layered, and, after the coagulation of agarose, the cells were cultured in a carbon dioxide incubator for 2 days. Culture medium in a volume of 1.5 ml with neutral red was layered, culture was performed overnight, and the number of viral plaques formed was then counted. The plaque count calculated from the maximum dilution rate that allowed plaque counting was employed, and the virus count was calculated.

(d) Histopathological Examination

The lung (left lung) excised was fixed, and a paraffin section was then produced for every case in each group in accordance with a conventional method. The paraffin sections were HE-stained. Microscopic examination was performed. Histopathological findings were scored in five grades. 0: no change (−), 1: very mild (+), 2: mild (+), 3: moderate (++), 4: severe (+++).

(e) Statistical Processing

For general condition scores, gross findings for the lung, viral plaque counts, and histopathological examination, mean and standard error were calculated for each group. Significance test was performed between the control group and the group with administration of the AM analog at low dose or high dose with use of Wilcoxon's rank sum test for general condition scores, gross findings for the lung, viral plaque counts, and histopathological examination. The significance level was set to 5%, and cases of less than 5% and those of less than 1% were separately shown.

[XI-4: Results]

Table 6 shows general condition scores for mice of different groups. Each value in the table is the mean and standard error of scores for the mice of the corresponding group. "*" in the table indicates the presence of significant difference from the control group (*:p<0.01).

TABLE 6

| | Control | Group with administration | |
| Group | group | of AM analog | |
| Dose (nmol/kg) | 0 | 10 | 100 |
| Number of animals | 8 | 8 | 8 |
| 1 day before inoculation | 0.0 ± 0.0 | 0.0 ± 0.0 | 0.0 ± 0.0 |
| Days after inoculation | | | |
| 0 | 0.0 ± 0.0 | 0.0 ± 0.0 | 0.0 ± 0.0 |
| 1 | 0.0 ± 0.0 | 0.0 ± 0.0 | 0.0 ± 0.0 |
| 2 | 0.3 ± 0.0 | 0.2 ± 0.0 | 0.1 ± 0.0* |
| 3 | 0.5 ± 0.0 | 0.5 ± 0.0 | 0.5 ± 0.0 |
| 4 | 0.8 ± 0.0 | 0.8 ± 0.0 | 0.8 ± 0.0 |
| 5 | 1.0 ± 0.0 | 1.0 ± 0.0 | 1.0 ± 0.0 |

General condition score

Table 7 shows scores of gross lesion examination of the lungs for different groups. Each value in the table is the mean and standard error of scores of gross lesion examination of the lungs for the mice of the corresponding group. "*" in the table indicates the presence of significant difference from the control group (*:p<0.01).

TABLE 7

Score of gross lesion examination of lung

| | Control | Group with administration | |
| Group | group | of AM analog | |
| Dose (nmol/kg) | 0 | 10 | 100 |
| Number of animals | 8 | 8 | 8 |
| Lung | | | |
| Left lung | 3.9 ± 0.1 | 2.8 ± 0.2* | 2.6 ± 0.2* |
| Right lung | 4.0 ± 0.0 | 2.9 ± 0.1* | 2.5 ± 0.2* |

Table 8 shows virus concentrations in the lung for different groups. Each value in the table is the mean and standard error of virus concentration ($\times 10^4$ PFU) in the right lung for the mice of the corresponding group. "*" in the table indicates the presence of significant difference from the control group (*:p<0.01).

TABLE 8

Virus concentration in lung

| | Control | Group with administration | |
| Group | group | of AM analog | |
| Dose (nmol/kg) | 0 | 10 | 100 |
| Number of animals | 8 | 8 | 8 |
| Virus concentration ($\times 10^4$ PFU/right lung) | 97.8 ± 3.4 | 53.0 ± 3.0* | 43.3 ± 4.6* |

For general condition scores, the group with administration of the AM analog at high dose exhibited a significantly lower value than the control group 2 days after ingestion (Table 6). For scores of gross lesion examination of the lungs, the groups with administration of the AM analog at high dose and at low dose each exhibited a significantly lower value than the control group for both the left and right lungs (Table 7). For virus counts in the right lung, the groups with administration of the AM analog at high dose and at low dose each exhibited significant reduction as compared with the control group (Table 8). For scores of histopathological examination, no significant difference from the control group was found for both of the groups with administration of the AM analog at high dose and at low dose.

The results of the present experiment suggested that AM analog peptides such as [Ala-44]hAM(13-52) exert effects of suppression of infectivity, inhibition of the progression of conditions, and so forth for viral infection caused by influenzavirus.

The invention is not limited to Examples shown above, and includes various modifications. For example, Examples shown above are detail description for easy-to-understand explanation of the invention, and not necessarily limited to the configuration including all the components described. In addition, some of the components in each Example may be supplemented with other components, deleted, and/or substituted.

All publications, patent and patent applications cited herein are incorporated herein by reference in their entirety.

The invention claimed is:

1. A compound or a salt thereof, or a solvate thereof, wherein the compound comprises a peptide selected from the group consisting of:

(a) a peptide comprising the amino acid sequence of SEQ ID NO: 3, wherein an amino acid residue(s) only at position 32 and/or 33 is substituted or deleted, and when the amino acid residue at position 32 is substituted, the amino acid residue at position 32 is substituted with one selected from the group consisting of D-arginine, lysine, alanine, glycine, aspartic acid, and phenylalanine;

(b) a peptide having a disulfide bond formed by cysteine residues at positions 4 and 9 of a peptide comprising the amino acid sequence of SEQ ID NO: 3 wherein an amino acid residue(s) only at position 32 and/or 33 is substituted or deleted, and when the amino acid residue at position 32 is substituted, the amino acid residue at position 32 is substituted with one selected from the group consisting of D-arginine, lysine, alanine, glycine, aspartic acid, and phenylalanine;

(c) a peptide wherein the disulfide bond of the peptide of (b) is substituted with an ethylene group;

(d) a peptide wherein any of the peptides of (a) to (c) is amidated at the C-terminus thereof; and (e) a peptide wherein any of the peptides of (a) to (c) has a glycine residue added to the C-terminus thereof.

2. The compound according to claim 1 or a salt thereof, or a solvate thereof, wherein, in the peptide of (a), only the amino acid residues at position 32 and 33 are substituted or deleted.

3. The compound according to claim 1 or a salt thereof, or a solvate thereof, wherein the compound comprises a peptide comprising the amino acid sequence of any of SEQ ID NOs: 4 to 11, being amidated at the C-terminus thereof, and having a disulfide bond formed by cysteine residues at positions 4 and 9.

4. A method for producing the compound according to claim 1 or a salt thereof, or a solvate thereof, the method comprising: a peptide chain synthesis step of synthesizing a peptide chain having an amino acid sequence of the compound according to claim 1 by peptide synthesis on solid phase system or in liquid phase system.

5. A pharmaceutical composition comprising the compound according to claim 1 or a pharmaceutically acceptable salt thereof, or a pharmaceutically acceptable solvate thereof and one or more pharmaceutically acceptable carriers.

6. The pharmaceutical composition according to claim 5 for use in the prevention or treatment of cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

7. A method for preventing or treating one or more conditions, diseases, and/or disorders selected from the group consisting of cardiovascular diseases, brain and nervous system diseases, gastrointestinal diseases, endocrine metabolic diseases, respiratory diseases, and other diseases, the method comprising administering an effective amount of the compound according to claim 1 or a pharmaceutically acceptable salt thereof, or a pharmaceutically acceptable solvate thereof to a subject in need of prevention or treatment of the conditions, diseases, and/or disorders.

8. The method according to claim 7, wherein the one or more conditions, diseases, and/or disorders are cardiac insufficiency, acute myocardial infarction, cardiac arrhythmia, atrial fibrillation, pulmonary hypertension, a peripheral vascular disease, cerebral infarction, dementia, inflammatory bowel disease, Crohn's disease, ulcerative colitis, intestinal tract Behcet's disease, diabetes, diabetic renal disease, diabetic retinopathy, pulmonary fibrosis, septicemia, septic shock, or a viral infection.

9. The compound according to claim 1 or a salt thereof, or a solvate thereof, wherein the peptide comprises the amino acid sequence of SEQ ID NO: 3 wherein the amino acid residue(s) only at position 32 and/or 33 is substituted or deleted one to three amino acid residues are substituted or deleted relative to SEQ ID NO: 3, having a disulfide bond formed by cysteine residues at positions 4 and 9 of the peptide, and the disulfide bond of the peptide of is substituted with an ethylene group.

10. The compound according to claim 1 or a salt thereof, or a solvate thereof, wherein the peptide comprises the amino acid sequence of SEQ ID NO: 4.

11. The compound according to claim 1 or a salt thereof, or a solvate thereof, wherein the peptide comprises the amino acid sequence of SEQ ID NO: 5.

12. The compound according to claim 1 or a salt thereof, or a solvate thereof, wherein the peptide comprises the amino acid sequence of SEQ ID NO: 6.

13. The compound according to claim 1 or a salt thereof, or a solvate thereof, wherein the peptide comprises the amino acid sequence of SEQ ID NO: 7.

14. The compound according to claim 1 or a salt thereof, or a solvate thereof, wherein the peptide comprises the amino acid sequence of SEQ ID NO: 8.

15. The compound according to claim 1 or a salt thereof, or a solvate thereof, wherein the peptide comprises the amino acid sequence of SEQ ID NO: 9.

16. The compound according to claim 1 or a salt thereof, or a solvate thereof, wherein the peptide comprises the amino acid sequence of SEQ ID NO: 10.

17. The compound according to claim 1 or a salt thereof, or a solvate thereof, wherein the peptide comprises the amino acid sequence of SEQ ID NO: 11.

18. The compound according to claim 1 or a salt thereof, or a solvate thereof, wherein the peptide comprises the amino acid sequence of SEQ ID NO: 3, and the amino acid residue only at position 32 of the SEQ ID NO: 3 is substituted or deleted.

19. The compound according to claim 1 or a salt thereof, or a solvate thereof, wherein the peptide comprises the amino acid sequence of SEQ ID NO: 3, and the amino acid residue only at position 33 of the SEQ ID NO: 3 is substituted or deleted.

20. The compound according to claim 1 or a salt thereof, or a solvate thereof, wherein the peptide comprises (b) the peptide having a disulfide bond formed by cysteine residues at positions 4 and 9 of a peptide comprising the amino acid sequence of SEQ ID NO: 3 wherein an amino acid residue(s) only at position 32 and/or 33 is substituted or deleted.

21. The compound according to claim 1 or a salt thereof, or a solvate thereof, wherein the peptide comprises (c) the peptide wherein the disulfide bond of the peptide of (b) is substituted with an ethylene group.

22. The compound according to claim 1 or a salt thereof, or a solvate thereof, wherein the peptide comprises (d) the peptide wherein any of the peptides of (a) to (c) is amidated at the C-terminus thereof.

23. The compound according to claim 1 or a salt thereof, or a solvate thereof, wherein the peptide comprises (e) the peptide wherein any of the peptides of (a) to (c) has a glycine residue added to the C-terminus thereof.

* * * * *

SEQUENCE LISTING

<160> NUMBER OF SEQ ID NOS: 11

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
        20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 2
<211> LENGTH: 32
<212> TYPE: PRT
<213> ORGANISM: Artificial
<220> FEATURE:
<223> OTHER INFORMATION: Synthetic

<400> SEQUENCE: 2

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Arg
        20                  25                  30

<210> SEQ ID NO 3
<211> LENGTH: 40
<212> TYPE: PRT
<213> ORGANISM: Artificial
<220> FEATURE:
<223> OTHER INFORMATION: Synthetic

<400> SEQUENCE: 3

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Arg
        20                  25                  30

Ser Lys Ile Ser Pro Gln Gly Tyr
        35                  40

<210> SEQ ID NO 4
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (32)..(32)
<223> OTHER INFORMATION: Xaa is D-Arg

<400> SEQUENCE: 4

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Xaa
        20                  25                  30

Ser Lys Ile Ser Pro Gln Gly Tyr
        35                  40

<210> SEQ ID NO 5
<211> LENGTH: 40
<212> TYPE: PRT
<213> ORGANISM: Artificial
<220> FEATURE:
<223> OTHER INFORMATION: Synthetic

<400> SEQUENCE: 5

Ser Phe Gly Cys Arg Phe Gly Thr Cys Thr Val Gln Lys Leu Ala His
1               5                   10                  15

```
Gln Ile Tyr Gln Phe Thr Asp Lys Asp Lys Asp Asn Val Ala Pro Lys
            20                  25                  30

Ser Lys Ile Ser Pro Gln Gly Tyr
            35                  40

<210> SEQ ID NO 6
<211> LENGTH: 40
<212> TYPE: PRT
<213> ORGANISM: Artificial
<220> FEATURE:
<223> OTHER INFORMATION: Synthetic

<400> SEQUENCE: 6

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Ala
            20                  25                  30

Ser Lys Ile Ser Pro Gln Gly Tyr
            35                  40

<210> SEQ ID NO 7
<211> LENGTH: 40
<212> TYPE: PRT
<213> ORGANISM: Artificial
<220> FEATURE:
<223> OTHER INFORMATION: Synthetic

<400> SEQUENCE: 7

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Gly
            20                  25                  30

Ser Lys Ile Ser Pro Gln Gly Tyr
            35                  40

<210> SEQ ID NO 8
<211> LENGTH: 39
<212> TYPE: PRT
<213> ORGANISM: Artificial
<220> FEATURE:
<223> OTHER INFORMATION: Synthetic

<400> SEQUENCE: 8

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Ser
            20                  25                  30

Lys Ile Ser Pro Gln Gly Tyr
            35

<210> SEQ ID NO 9
<211> LENGTH: 40
<212> TYPE: PRT
<213> ORGANISM: Artificial
<220> FEATURE:
<223> OTHER INFORMATION: Synthetic

<400> SEQUENCE: 9

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Asp
            20                  25                  30
```

```
Ser Lys Ile Ser Pro Gln Gly Tyr
        35                  40

<210> SEQ ID NO 10
<211> LENGTH: 40
<212> TYPE: PRT
<213> ORGANISM: Artificial
<220> FEATURE:
<223> OTHER INFORMATION: Synthetic

<400> SEQUENCE: 10

Ser Phe Gly Cys Arg Phe Gly Thr Cys Thr Val Gln Lys Leu Ala His
1               5               10                  15

Gln Ile Tyr Gln Phe Thr Asp Lys Asp Lys Asp Asn Val Ala Pro Phe
            20              25                  30

Ser Lys Ile Ser Pro Gln Gly Tyr
        35                  40

<210> SEQ ID NO 11
<211> LENGTH: 40
<212> TYPE: PRT
<213> ORGANISM: Artificial
<220> FEATURE:
<223> OTHER INFORMATION: Synthetic

<400> SEQUENCE: 11

Ser Phe Gly Cys Arg Phe Gly Thr Cys Thr Val Gln Lys Leu Ala His
1               5               10                  15

Gln Ile Tyr Gln Phe Thr Asp Lys Asp Lys Asp Asn Val Ala Pro Arg
            20              25                  30

Pro Lys Ile Ser Pro Gln Gly Tyr
        35                  40
```